US008722041B2

(12) United States Patent
Sandvold et al.

(10) Patent No.: US 8,722,041 B2
(45) Date of Patent: May 13, 2014

(54) ANTI-HUMAN EQUILIBRATIVE NUCLEOSIDE TRANSPORTER 1 (HENT1) ANTIBODIES AND METHODS OF USE THEREOF

(75) Inventors: Marit L. Sandvold, Porsgrunn (NO); Finn Myhren, Porsgrunn (NO); Carol E. Cass, Edmonton (CA); James D. Young, Edmonton (CA)

(73) Assignee: Governors of the University of Alberta, Edmonton (CA)

( * ) Notice: Subject to any disclaimer, the term of this patent is extended or adjusted under 35 U.S.C. 154(b) by 0 days.

(21) Appl. No.: 13/161,941

(22) Filed: Jun. 16, 2011

(65) Prior Publication Data

US 2012/0009197 A1 Jan. 12, 2012

Related U.S. Application Data

(60) Provisional application No. 61/355,357, filed on Jun. 16, 2010, provisional application No. 61/432,702, filed on Jan. 14, 2011.

(51) Int. Cl.
*A61K 38/00* (2006.01)
*C07K 14/47* (2006.01)
*C07K 16/28* (2006.01)

(52) U.S. Cl.
USPC .......... 424/130.1; 424/133.1; 424/138.1; 424/141.1; 424/142.1; 530/350; 530/388.1; 530/389.1

(58) Field of Classification Search
None
See application file for complete search history.

(56) References Cited

FOREIGN PATENT DOCUMENTS

WO   WO-98/29437     7/1998
WO   WO-2011/121453  10/2011

OTHER PUBLICATIONS

Lederman, 1991, Molecular Immunology, vol. 28, No. 11, pp. 1171-1181.*
Li, 1980, PNAS, vol. 77, No. 6, pp. 3211-3214.*

Adema et al., "Fatty acid derivatives of cytarabine and gemcitabine, CP-4055 and CP-4126, show a prolonged cellular retention compared to the parent drug," Proceedings of the 99th Annual Meeting of the American Association for Cancer Research. Abstract nr 5740 (2008).
Breistol, et al., "Antitumor activity of P-4055 (elaidic acid-cytarabine) compared to cytarabine in metastatic and s.c. human tumor xenograft models," Cancer Res 59 (1999) 2944-2949.
Brueckner, et al., "Delivery of 5-azacytidine to human cancer cells by elaidic acid esterification increases therapeutic drug efficacy," Mol Cancer Ther., vol. 9(5): 1256-1264 (2010).
Farrell, et al., "Human Equilibrative Nucleoside Transporter 1 Levels Predict Response to Gemcitabine in Patients With Pancreatic Cancer," Gastroenterology 136 (2009) 187-195.
Galmarini, et al., "Potential mechanisms of resistance to cytarabine in AML patients," Leuk Res 26 (2002) 621-629.
Galmarini et al., "CP-4055 and CP-4126 are active in ara-C and gemcitabine-resistant lymphoma cell lines," Br J Haematol 144 (2009) 273-275.
Giovannetti, et al., "Transcription analysis of human equilibrative nucleoside transporter-1 predicts survival in pancreas cancer patients treated with gemcitabine," Cancer Res 66 (2006) 3928-3935).
Ibarra et al., "Reduced ribavirin antiviral efficacy via nucleoside transporter-mediated drug resistance," J. Virol., vol. 83(9): 4583-47 (2009).
Jennings et al., "Distinct regional distribution of human equilibrative nucleoside transporter proteins 1 and 2 (hENT1 and hENT2) in the central nervous system," Neuropharmacology, vol. 40(5): 722-731 (2001).
Quashie et al., "Uptake of purines in Plasmodium falciparum-infected human erythrocytes is mostly mediated by the human equilibrative nucleoside transporter and the human facilitative nucleobase transporter," Malaria Journal, vol. 9: 36 (2010).

* cited by examiner

*Primary Examiner* — Robert Landsman
*Assistant Examiner* — Ian Dang
(74) *Attorney, Agent, or Firm* — Mintz Levin Cohn Ferris Glovsky and Popeo, P.C.; Ivor R. Elrifi

(57) ABSTRACT

This invention provides monoclonal antibodies that recognize hENT1. The invention further provides methods of using such monoclonal antibodies as a therapeutic, diagnostic, and/or prophylactic in disorders associated with aberrant hENT1 expression and/or activity.

9 Claims, 3 Drawing Sheets

|  | x2 | x | b |
|---|---|---|---|
| coefficient | 8.5482 | 15.493 | -0.9335 |

Range from 1.0-0.2 (450nm)

| sample | dilution | read1 | read 2 | read3 | average | conc [ng/well]* |
|---|---|---|---|---|---|---|
| Sup 1 1:10 | 10 | 0.0800 | 0.0830 | 0.0930 | 0.0853 | 4.5082 |
| Sup 2 1:10 | 10 | 0.3120 | 0.3060 | 0.3070 | 0.3083 | 46.5618 |
| Sup 3 1:10 | 10 | 0.1530 | 0.1630 | 0.1650 | 0.1603 | 17.7029 |

* 1 well is 100μl

SEQUENCE LISTING

<160> NUMBER OF SEQ ID NOS: 59

<210> SEQ ID NO 1
<211> LENGTH: 494
<212> TYPE: DNA
<213> ORGANISM: Artificial Sequence
<220> FEATURE:
<223> OTHER INFORMATION: chemically synthesized

<400> SEQUENCE: 1

```
atggaatgca cctgggtttt tctcttcctc ctgtcagtaa ttgcaggtgt ccaatcccag      60
gttcatctgc agcagtctgg ggctgagctg gtgaggcctg gggcttcagt gacgccgccc     120
tgcaaggctt cgggctacac atttactgac tatgaaatgc actgggtgaa acagacacct     180
gtgcatggcc tggaatggat tggcgctatt gatcctgaaa ctggtgctat tgtctacaat     240
cagaagttca agggcaaggc cacactgact gcagacaaat cctccaacac agcccacatg     300
gagctccgca gcctgacatc tgaggactct gccgtctatt actgtacaag agagtttact     360
tactggggcc aagggactct ggtcactgtc tctgcagcca aaacgacacc cccatccgtc     420
ttccccctgg cacaagccaa attctgcaga tatccatcac actggcggcc gctcgagcat     480
ctattctttg ggaa                                                       494
```

<210> SEQ ID NO 2
<211> LENGTH: 164
<212> TYPE: PRT
<213> ORGANISM: Artificial Sequence
<220> FEATURE:
<223> OTHER INFORMATION: chemically synthesized

<400> SEQUENCE: 2

Met Glu Cys Thr Trp Val Phe Leu Phe Leu Ser Val Ile Ala Gly
1               5                   10                  15

Val Gln Ser Gln Val His Leu Gln Gln Ser Gly Ala Glu Leu Val Arg
            20                  25                  30

Pro Gly Ala Ser Val Thr Pro Pro Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Ala Ile Val Tyr Asn
65                  70                  75                  80

Gln Lys Phe Lys Gly Lys Ala Thr Leu Thr Ala Asp Lys Ser Ser Asn
                85                  90                  95

Thr Ala His Met Glu Leu Arg Ser Leu Thr Ser Glu Asp Ser Ala Val
            100                 105                 110

Tyr Tyr Cys Thr Arg Glu Phe Thr Tyr Trp Gly Gln Gly Thr Leu Val

Thr Val Ser Ala Ala Lys Thr Thr Pro Pro Ser Val Phe Pro Leu Ala
            130                 135                 140

Gln Ala Lys Phe Cys Arg Tyr Pro Ser His Trp Arg Pro Leu Glu His
145                 150                 155                 160

Leu Phe Phe Gly

<210> SEQ ID NO 3
<211> LENGTH: 447
<212> TYPE: DNA
<213> ORGANISM: Artificial Sequence
<220> FEATURE:
<223> OTHER INFORMATION: chemically synthesized

<400> SEQUENCE: 3
atggaatgca cctgggttat tctcttcctc ctgtcagtaa ttgcaggtgt ccaatcccag      60
gttcatctgc agcagtctgg ggctgagctg gtgaggcctg gggcttcagt gacgctgccc     120
tgcaaggctt cgggctacac atttactgac atgaaatgc actgggtgaa acagacacct     180
gtgcatggcc tggaatggat cggcgctatt gatcctgaaa ctggtgctat tgtctacaat     240
cagaagctca agggcaaggc cacactggct gcagacaaat cctccaacac agcctacatg     300
gagctccgca gcctgacatc tgaggactct gccgtctatt actgtacaag agagtttact     360
tactggggcc aagggactct ggtcactgtc tctgcagcca aaacgacacc cccaccc gtt     420 tatccactgg cccccctgga agcttggg                                        447

<210> SEQ ID NO 4
<211> LENGTH: 149
<212> TYPE: PRT
<213> ORGANISM: Artificial Sequence
<220> FEATURE:
<223> OTHER INFORMATION: chemically synthesized

<400> SEQUENCE: 4

Met Glu Cys Thr Trp Val Ile Leu Phe Leu Leu Ser Val Ile Ala Gly
1               5                   10                  15

Val Gln Ser Gln Val His Leu Gln Gln Ser Gly Ala Glu Leu Val Arg
            20                  25                  30

Pro Gly Ala Ser Val Thr Leu Pro Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Ala Ile Val Tyr Asn
65                  70                  75                  80

Gln Lys Leu Lys Gly Lys Ala Thr Leu Ala Ala Asp Lys Ser Ser Asn
                85                  90                  95

Thr Ala Tyr Met Glu Leu Arg Ser Leu Thr Ser Glu Asp Ser Ala Val
            100                 105                 110

Tyr Tyr Cys Thr Arg Glu Phe Thr Tyr Trp Gly Gln Gly Thr Leu Val
        115                 120                 125

Thr Val Ser Ala Ala Lys Thr Thr Pro Pro Val Tyr Pro Leu Ala
    130                 135                 140

Pro Trp Lys Leu Gly
145

<210> SEQ ID NO 5
<211> LENGTH: 446
<212> TYPE: DNA

```
<213> ORGANISM: Artificial Sequence
<220> FEATURE:
<223> OTHER INFORMATION: chemically synthesized

<400> SEQUENCE: 5
atgaaatgga cctgggtttt cctcttcctc ctgtcagtaa ttgcaggtgt ccaatcccag      60
gttcatctgc agcagtctgg ggctgagctg gtgaggcctg gggcttcagt gacgctgccc     120
tgcaaggctt cgggctacac atttactgac tatgaaatgc actgggtgaa acagacacct     180
gtgcatggcc tggaatggat tggcgctatt gatcctgaaa ctggtgctat tgtctacaat     240
cagaagttca gggcaaggc cacactgact gcagacaaat cctccaacac agcctacatg      300
gagctccgca gcctgacatc tgaggactct gccgtctatt actgtacaag agagtttact     360
tactggggcc aagggactct ggtcactgtc tctgcagcca aaacgacacc cccatccgtt     420
tatccactgg cccctggaag cttggg                                          446

<210> SEQ ID NO 6
<211> LENGTH: 148
<212> TYPE: PRT
<213> ORGANISM: Artificial Sequence
<220> FEATURE:
<223> OTHER INFORMATION: chemically synthesized

<400> SEQUENCE: 6

Met Lys Trp Thr Trp Val Phe Leu Phe Leu Leu Ser Val Ile Ala Gly
1               5                   10                  15

Val Gln Ser Gln Val His Leu Gln Gln Ser Gly Ala Glu Leu Val Arg
            20                  25                  30

Pro Gly Ala Ser Val Thr Leu Pro Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Ala Ile Val Tyr Asn
65                  70                  75                  80

Gln Lys Phe Lys Gly Lys Ala Thr Leu Thr Ala Asp Lys Ser Ser Asn
                85                  90                  95

Thr Ala Tyr Met Glu Leu Arg Ser Leu Thr Ser Glu Asp Ser Ala Val
            100                 105                 110

Tyr Tyr Cys Thr Arg Glu Phe Thr Tyr Trp Gly Gln Gly Thr Leu Val
        115                 120                 125

Thr Val Ser Ala Ala Lys Thr Thr Pro Pro Ser Val Tyr Pro Leu Ala
    130                 135                 140

Pro Gly Ser Leu
145

<210> SEQ ID NO 7
<211> LENGTH: 446
<212> TYPE: DNA
<213> ORGANISM: Artificial Sequence
<220> FEATURE:
<223> OTHER INFORMATION: chemically synthesized

<400> SEQUENCE: 7
atggaatgca gcagggttat tctcttcctc ctgtcagtaa ttgcaggtgt ccaatcccag      60
gttcatctgc agcagtctgg ggctgagctg gtgaggcctg gggcttcagt gacgctgccc     120
tgcaaggctt cgggctacac atttactgac tatgaaatgc actgggtgaa acagacacct     180
gtgcatggcc tggaatggat tggcgctatt gatcctgaaa ctggtgctat tgtctacaat     240
```

```
cagaagttca agggcaaggc cacactgact gcagacaaat cctccaacac agcctacatg      300
gagctccgca gcctgacatc tgaggactct gccgtctatt actgtacaag agagtttact      360
tactggggcc aagggactct ggtcactgtc tctgcagcca aaacgacacc cccacccgtc      420 tatccccctgg cccctggaag cttggg                                          446
```

<210> SEQ ID NO 8
<211> LENGTH: 148
<212> TYPE: PRT
<213> ORGANISM: Artificial Sequence
<220> FEATURE:
<223> OTHER INFORMATION: chemically synthesized

<400> SEQUENCE: 8

```
Met Glu Cys Ser Arg Val Ile Leu Phe Leu Leu Ser Val Ile Ala Gly
1               5                   10                  15

Val Gln Ser Gln Val His Leu Gln Gln Ser Gly Ala Glu Leu Val Arg
            20                  25                  30

Pro Gly Ala Ser Val Thr Leu Pro Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Ala Ile Val Tyr Asn
65                  70                  75                  80

Gln Lys Phe Lys Gly Lys Ala Thr Leu Thr Ala Asp Lys Ser Ser Asn
                85                  90                  95

Thr Ala Tyr Met Glu Leu Arg Ser Leu Thr Ser Glu Asp Ser Ala Val
            100                 105                 110

Tyr Tyr Cys Thr Arg Glu Phe Thr Tyr Trp Gly Gln Gly Thr Leu Val
        115                 120                 125

Thr Val Ser Ala Ala Lys Thr Thr Pro Pro Val Tyr Pro Leu Ala
    130                 135                 140

Pro Gly Ser Leu
145
```

<210> SEQ ID NO 9
<211> LENGTH: 148
<212> TYPE: PRT
<213> ORGANISM: Artificial Sequence
<220> FEATURE:
<223> OTHER INFORMATION: chemically synthesized

<400> SEQUENCE: 9

```
Met Glu Cys Thr Trp Val Ile Leu Phe Leu Leu Ser Val Ile Ala Gly
1               5                   10                  15

Val Gln Ser Gln Val His Leu Gln Gln Ser Gly Ala Glu Leu Val Arg
            20                  25                  30

Pro Gly Ala Ser Val Thr Leu Pro Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Ala Ile Val Tyr Asn
65                  70                  75                  80

Gln Lys Phe Lys Gly Lys Ala Thr Leu Thr Ala Asp Lys Ser Ser Asn
                85                  90                  95

Thr Ala Tyr Met Glu Leu Arg Ser Leu Thr Ser Glu Asp Ser Ala Val
            100                 105                 110

Tyr Tyr Cys Thr Arg Glu Phe Thr Tyr Trp Gly Gln Gly Thr Leu Val
```

```
                        115                 120                 125
Thr Val Ser Ala Ala Lys Thr Thr Pro Pro Ser Val Tyr Pro Leu Ala
                    130                 135                 140

Pro Gly Ser Leu
145

<210> SEQ ID NO 10
<211> LENGTH: 8
<212> TYPE: PRT
<213> ORGANISM: Artificial Sequence
<220> FEATURE:
<223> OTHER INFORMATION: chemically synthesized

<400> SEQUENCE: 10

Gly Tyr Thr Phe Thr Asp Tyr Glu
1               5

<210> SEQ ID NO 11
<211> LENGTH: 8
<212> TYPE: PRT
<213> ORGANISM: Artificial Sequence
<220> FEATURE:
<223> OTHER INFORMATION: chemically synthesized

<400> SEQUENCE: 11

Ile Asp Pro Glu Thr Gly Ala Ile
1               5

<210> SEQ ID NO 12
<211> LENGTH: 6
<212> TYPE: PRT
<213> ORGANISM: Artificial Sequence
<220> FEATURE:
<223> OTHER INFORMATION: chemically synthesized

<400> SEQUENCE: 12

Thr Arg Glu Phe Thr Tyr
1               5

<210> SEQ ID NO 13
<211> LENGTH: 357
<212> TYPE: DNA
<213> ORGANISM: Artificial Sequence
<220> FEATURE:
<223> OTHER INFORMATION: chemically synthesized

<400> SEQUENCE: 13
tctcctttca acaaagcaca tttcgatttc cagcttggtg cctccaccga acgtccacgg      60
aaaatgtgta ccttgcacgc agtaataaac tcccaaatcc tcagcctcca ctctgctgat     120
tttcagtgaa aaatctgttc ctgaaccagt gccagtgaac ctgtcaggga ctccagagtt     180
cagtttagac accagataga ttaggcgctt tggagactgg cctggcctct gaaataacca     240
attcaagtag gttttttccat tactaaataa gaggctctga cttgacctgc aagagacaga     300
ggctggttgt ccaatggtaa ccgacaaagt gagtggagtt tgggtcatca aaacatc        357

<210> SEQ ID NO 14
<211> LENGTH: 119
<212> TYPE: PRT
<213> ORGANISM: Artificial Sequence
<220> FEATURE:
<223> OTHER INFORMATION: chemically synthesized

<400> SEQUENCE: 14

Asp Val Leu Met Thr Gln Thr Pro Leu Thr Leu Ser Val Thr Ile Gly
```

```
1               5                  10                 15
Gln Pro Ala Ser Val Ser Cys Arg Ser Ser Gln Ser Leu Leu Phe Ser
            20                  25                 30

Asn Gly Lys Thr Tyr Leu Asn Trp Leu Phe Gln Arg Pro Gly Gln Ser
            35                  40                 45

Pro Lys Arg Leu Ile Tyr Leu Val Ser Lys Leu Asn Ser Gly Val Pro
 50                  55                  60

Asp Arg Phe Thr Gly Thr Gly Ser Gly Thr Asp Phe Ser Leu Lys Ile
 65                  70                  75                  80

Ser Arg Val Glu Ala Glu Asp Leu Gly Val Tyr Tyr Cys Val Gln Gly
            85                  90                 95

Thr His Phe Pro Trp Thr Phe Gly Gly Gly Thr Lys Leu Glu Ile Glu
            100                 105                110

Met Cys Phe Val Glu Arg Arg
            115

<210> SEQ ID NO 15
<211> LENGTH: 367
<212> TYPE: DNA
<213> ORGANISM: Artificial Sequence
<220> FEATURE:
<223> OTHER INFORMATION: chemically synthesized

<400> SEQUENCE: 15
attggatatc ctcgcagcat ctcggcttga tgttttgatg acccaaactc cactcacttt    60
gtcggttacc attggacaac cagcctctgt ctcttgcagg tcaagtcaga gcctcttatt   120
tagtaatgga aaaacctatt tgaattggtt atttcagagg ccaggccagt ctccaaagcg   180
cctaatctat ctggtgtcta aactgaactc tggagtccct gacaggttca ctggcactgg   240
ttcaggaaca gattttcac tgaaaatcag cagagtggag gctgaggatt tgggagttta   300
ttactgcgtg caaggtacac attttccgtg gacgttcggt ggaggcacca agctggaaat   360
caaacgg                                                              367

<210> SEQ ID NO 16
<211> LENGTH: 122
<212> TYPE: PRT
<213> ORGANISM: Artificial Sequence
<220> FEATURE:
<223> OTHER INFORMATION: chemically synthesized

<400> SEQUENCE: 16

Leu Asp Ile Leu Ala Ala Ser Arg Leu Asp Val Leu Met Thr Gln Thr
 1               5                  10                 15

Pro Leu Thr Leu Ser Val Thr Ile Gly Gln Pro Ala Ser Val Ser Cys
            20                  25                 30

Arg Ser Ser Gln Ser Leu Leu Phe Ser Asn Gly Lys Thr Tyr Leu Asn
            35                  40                 45

Trp Leu Phe Gln Arg Pro Gly Gln Ser Pro Lys Arg Leu Ile Tyr Leu
 50                  55                  60

Val Ser Lys Leu Asn Ser Gly Val Pro Asp Arg Phe Thr Gly Thr Gly
 65                  70                  75                  80

Ser Gly Thr Asp Phe Ser Leu Lys Ile Ser Arg Val Glu Ala Glu Asp
            85                  90                 95

Leu Gly Val Tyr Tyr Cys Val Gln Gly Thr His Phe Pro Trp Thr Phe
            100                 105                110

Gly Gly Gly Thr Lys Leu Glu Ile Lys Arg
            115                 120
```

<210> SEQ ID NO 17
<211> LENGTH: 374
<212> TYPE: DNA
<213> ORGANISM: Artificial Sequence
<220> FEATURE:
<223> OTHER INFORMATION: chemically synthesized

<400> SEQUENCE: 17

```
ctttcgcgat gatccttgca cgcatttcag gcttggatgt tttgatgacc caaactccac      60
tcactttgtc ggttaccatt ggacaaccag cctctgtctc ttgcaggtca agtcagagcc     120
tcttatttag taatggaaaa acctatttga attggttatt tcagaggcca ggccagtctc     180
caaagcgcct aatctgtctg tgtctaaac tgaactctgg agtccctgac aggttcactg      240
gcactggttc aggaacagat ttttcactga aaatcagcag agtggaggct gaggatttgg     300
gattttatta ctgcgtgcaa ggtacacatt ttccgtggac gttcggtgga ggcaccaagc     360
tggaaatcaa acgg                                                       374
```

<210> SEQ ID NO 18
<211> LENGTH: 124
<212> TYPE: PRT
<213> ORGANISM: Artificial Sequence
<220> FEATURE:
<223> OTHER INFORMATION: chemically synthesized

<400> SEQUENCE: 18

Phe Ala Met Ile Leu Ala Arg Ile Ser Gly Leu Asp Val Leu Met Thr
1               5                   10                  15

Gln Thr Pro Leu Thr Leu Ser Val Thr Ile Gly Gln Pro Ala Ser Val
            20                  25                  30

Ser Cys Arg Ser Ser Gln Ser Leu Leu Phe Ser Asn Gly Lys Thr Tyr
        35                  40                  45

Leu Asn Trp Leu Phe Gln Arg Pro Gly Gln Ser Pro Lys Arg Leu Ile
    50                  55                  60

Cys Leu Val Ser Lys Leu Asn Ser Gly Val Pro Asp Arg Phe Thr Gly
65                  70                  75                  80

Thr Gly Ser Gly Thr Asp Phe Ser Leu Lys Ile Ser Arg Val Glu Ala
                85                  90                  95

Glu Asp Leu Gly Phe Tyr Tyr Cys Val Gln Gly Thr His Phe Pro Trp
            100                 105                 110

Thr Phe Gly Gly Gly Thr Lys Leu Glu Ile Lys Arg
        115                 120

<210> SEQ ID NO 19
<211> LENGTH: 391
<212> TYPE: DNA
<213> ORGANISM: Artificial Sequence
<220> FEATURE:
<223> OTHER INFORMATION: chemically synthesized

<400> SEQUENCE: 19

```
gatgttttga tgacccaaac tccactcact ttgtcggtta ccattggaca accagcctct      60
gtctcttgca ggtcaagtca gagcctctta tttagtaatg gaaaaaccta tttgaattgg     120
ttatttcaga ggccaggcca gtctccaaag cgcctaatct atctggtgtc taaactgaac     180
tctggagtct ctgacaggtt cactggcact ggttcagaaa cagatttttc actgaaaatc     240
agcagagtgg aggctgagga tttgggagtt tattactgcg tgcaaggtac atattttccg     300
tggacgttcg gtggaggcac caagctggaa atcaaacggc ctttttaat tctgcagata     360
```

```
tcctatcaca acgttgctgg ccgcggccgc t                                 391
```

```
<210> SEQ ID NO 20
<211> LENGTH: 130
<212> TYPE: PRT
<213> ORGANISM: Artificial Sequence
<220> FEATURE:
<223> OTHER INFORMATION: chemically synthesized

<400> SEQUENCE: 20

Asp Val Leu Met Thr Gln Thr Pro Leu Thr Leu Ser Val Thr Ile Gly
1               5                   10                  15

Gln Pro Ala Ser Val Ser Cys Arg Ser Ser Gln Ser Leu Leu Phe Ser
            20                  25                  30

Asn Gly Lys Thr Tyr Leu Asn Trp Leu Phe Gln Arg Pro Gly Gln Ser
        35                  40                  45

Pro Lys Arg Leu Ile Tyr Leu Val Ser Lys Leu Asn Ser Gly Val Ser
    50                  55                  60

Asp Arg Phe Thr Gly Thr Gly Ser Glu Thr Asp Phe Ser Leu Lys Ile
65                  70                  75                  80

Ser Arg Val Glu Ala Glu Asp Leu Gly Val Tyr Tyr Cys Val Gln Gly
                85                  90                  95

Thr Tyr Phe Pro Trp Thr Phe Gly Gly Gly Thr Lys Leu Glu Ile Lys
            100                 105                 110

Arg Pro Phe Leu Ile Leu Gln Ile Ser Tyr His Asn Val Ala Gly Arg
        115                 120                 125

Gly Arg
    130
```

```
<210> SEQ ID NO 21
<211> LENGTH: 343
<212> TYPE: DNA
<213> ORGANISM: Artificial Sequence
<220> FEATURE:
<223> OTHER INFORMATION: chemically synthesized

<400> SEQUENCE: 21
gatgttttga tgacccaaac tccactcact ttgtcggtta ccattggaca accagcctct     60
gtctcttgca ggtcaagtca gagcctctta tttagtaatg gaaaaaccta tttgaattgg    120
ttatttcaga ggccaggcca gtctccaaag cgcctaatct atctggtgtc taaactgaac    180
tctggagtcc ctgacaggtt caccggcact ggttcaggaa cagattttcc actgaaaatc    240
agcagagtgg aggctgagga tttgggagtt tattactgcg tgcaaggtac acattttccg    300
tggacgttcg gtgccctttt taaggaggc cgtgataaaa aat                       343
```

```
<210> SEQ ID NO 22
<211> LENGTH: 114
<212> TYPE: PRT
<213> ORGANISM: Artificial Sequence
<220> FEATURE:
<223> OTHER INFORMATION: chemically synthesized

<400> SEQUENCE: 22

Asp Val Leu Met Thr Gln Thr Pro Leu Thr Leu Ser Val Thr Ile Gly
1               5                   10                  15

Gln Pro Ala Ser Val Ser Cys Arg Ser Ser Gln Ser Leu Leu Phe Ser
            20                  25                  30

Asn Gly Lys Thr Tyr Leu Asn Trp Leu Phe Gln Arg Pro Gly Gln Ser
        35                  40                  45
```

```
Pro Lys Arg Leu Ile Tyr Leu Val Ser Lys Leu Asn Ser Gly Val Pro
        50                  55                  60

Asp Arg Phe Thr Gly Thr Gly Ser Gly Thr Asp Phe Pro Leu Lys Ile
 65                  70                  75                  80

Ser Arg Val Glu Ala Glu Asp Leu Gly Val Tyr Tyr Cys Val Gln Gly
                 85                  90                  95

Thr His Phe Pro Trp Thr Phe Gly Ala Leu Phe Lys Gly Gly Arg Asp
                100                 105                 110

Lys Lys

<210> SEQ ID NO 23
<211> LENGTH: 113
<212> TYPE: PRT
<213> ORGANISM: Artificial Sequence
<220> FEATURE:
<223> OTHER INFORMATION: chemically synthesized

<400> SEQUENCE: 23

Asp Val Leu Met Thr Gln Thr Pro Leu Thr Leu Ser Val Thr Ile Gly
 1               5                  10                  15

Gln Pro Ala Ser Val Ser Cys Arg Ser Ser Gln Ser Leu Leu Phe Ser
                20                  25                  30

Asn Gly Lys Thr Tyr Leu Asn Trp Leu Phe Gln Arg Pro Gly Gln Ser
            35                  40                  45

Pro Lys Arg Leu Ile Tyr Leu Val Ser Lys Leu Asn Ser Gly Val Pro
        50                  55                  60

Asp Arg Phe Thr Gly Thr Gly Ser Gly Thr Asp Phe Ser Leu Lys Ile
 65                  70                  75                  80

Ser Arg Val Glu Ala Glu Asp Leu Gly Val Tyr Tyr Cys Val Gln Gly
                 85                  90                  95

Thr His Phe Pro Trp Thr Phe Gly Gly Gly Thr Lys Leu Glu Ile Lys
                100                 105                 110

Arg

<210> SEQ ID NO 24
<211> LENGTH: 11
<212> TYPE: PRT
<213> ORGANISM: Artificial Sequence
<220> FEATURE:
<223> OTHER INFORMATION: chemically synthesized

<400> SEQUENCE: 24

Gln Ser Leu Leu Phe Ser Asn Gly Lys Thr Tyr
 1               5                  10

<210> SEQ ID NO 25
<211> LENGTH: 3
<212> TYPE: PRT
<213> ORGANISM: Artificial Sequence
<220> FEATURE:
<223> OTHER INFORMATION: chemically synthesized

<400> SEQUENCE: 25

Leu Val Ser
 1

<210> SEQ ID NO 26
<211> LENGTH: 9
<212> TYPE: PRT
<213> ORGANISM: Artificial Sequence
<220> FEATURE:
```

-continued

<223> OTHER INFORMATION: chemically synthesized

<400> SEQUENCE: 26

Val Gln Gly Thr His Phe Pro Trp Thr
1               5

<210> SEQ ID NO 27
<211> LENGTH: 433
<212> TYPE: DNA
<213> ORGANISM: Artificial Sequence
<220> FEATURE:
<223> OTHER INFORMATION: chemically synthesized

<400> SEQUENCE: 27

```
atgaaatgca gctgggtttt cctcttcctc ctgtcagtaa ttgcaggtgt ccaatcccgg    60
gttcaactgc agcagtctgg gtctgagctg gtgaggcctg ggcttcagt gacgctgtcc   120
tgcaaggctt cgggctacac atttactgac tatgaaatgc actgggtgaa gcagacacct   180
gtgcatggcc tggaatggat tggagcgatt gatcctgaaa ctggtaaaac tgcctacaat   240
cagaagttca gggcaagac cacactgact gcagacaaat cctccagcac agcctacatg   300
gagttccgca gcctgacatc tgaggactct gccgtccatt actgtacaag agagttgact   360
tactggggcc aagggactct ggtcactgtc tctgcagcca aaacgacacc cccatcggtc   420
ttccccctgg cac                                                     433
```

<210> SEQ ID NO 28
<211> LENGTH: 144
<212> TYPE: PRT
<213> ORGANISM: Artificial Sequence
<220> FEATURE:
<223> OTHER INFORMATION: chemically synthesized

<400> SEQUENCE: 28

Met Lys Cys Ser Trp Val Phe Leu Phe Leu Leu Ser Val Ile Ala Gly
1               5                   10                  15

Val Gln Ser Arg Val Gln Leu Gln Gln Ser Gly Ser Glu Leu Val Arg
                20                  25                  30

Pro Gly Ala Ser Val Thr Leu Ser Cys Lys Ala Ser Gly Tyr Thr Phe
            35                  40                  45

Thr Asp Tyr Glu Met His Trp Val Lys Gln Thr Pro Val His Gly Leu
        50                  55                  60

Glu Trp Ile Gly Ala Ile Asp Pro Glu Thr Gly Lys Thr Ala Tyr Asn
65                  70                  75                  80

Gln Lys Phe Lys Gly Lys Thr Thr Leu Thr Ala Asp Lys Ser Ser Ser
                85                  90                  95

Thr Ala Tyr Met Glu Phe Arg Ser Leu Thr Ser Glu Asp Ser Ala Val
            100                 105                 110

His Tyr Cys Thr Arg Glu Leu Thr Tyr Trp Gly Gln Gly Thr Leu Val
        115                 120                 125

Thr Val Ser Ala Ala Lys Thr Thr Pro Pro Ser Val Phe Pro Leu Ala
    130                 135                 140

<210> SEQ ID NO 29
<211> LENGTH: 433
<212> TYPE: DNA
<213> ORGANISM: Artificial Sequence
<220> FEATURE:
<223> OTHER INFORMATION: chemically synthesized

<400> SEQUENCE: 29

```
atggaatgca cctgggtttt cctcttcctc ctgtcagtaa ttgcaggtgt ccaatcccag    60
gttcaactgc agcagtctgg gtctgagctg gtgaggcctg ggcttcagt gacgctgtcc    120 tgcaaggctt cgggctacac atttactgac tatgaaatgc actgggtgga gcagacacct   180
gtgcatggcc tggaatggat tggagcgatt gatcctgaaa ctggtaaaac tgcctacaat   240
cagaagttca aggcaagac cacactgact gcagacaaat cctccagcac agcctacatg    300
gagttccgca gcctgacatc tgaggactct gccgtccatt actgtacaag agagttgact   360
tactggggcc aagggactct ggtcactgtc tctgcagcca aaacgacacc cccatccgtc   420
ttccccctgg cac                                                      433
```

<210> SEQ ID NO 30
<211> LENGTH: 144
<212> TYPE: PRT
<213> ORGANISM: Artificial Sequence
<220> FEATURE:
<223> OTHER INFORMATION: chemically synthesized

<400> SEQUENCE: 30

```
Met Glu Cys Thr Trp Val Phe Leu Phe Leu Leu Ser Val Ile Ala Gly
1               5                   10                  15

Val Gln Ser Gln Val Gln Leu Gln Gln Ser Gly Ser Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Glu Met His Trp Val Glu Gln Thr Pro Val His Gly Leu
    50                  55                  60

Glu Trp Ile Gly Ala Ile Asp Pro Glu Thr Gly Lys Thr Ala Tyr Asn
65                  70                  75                  80

Gln Lys Phe Lys Gly Lys Thr Thr Leu Thr Ala Asp Lys Ser Ser Ser
                85                  90                  95

Thr Ala Tyr Met Glu Phe Arg Ser Leu Thr Ser Glu Asp Ser Ala Val
            100                 105                 110

His Tyr Cys Thr Arg Glu Leu Thr Tyr Trp Gly Gln Gly Thr Leu Val
        115                 120                 125

Thr Val Ser Ala Ala Lys Thr Thr Pro Pro Ser Val Phe Pro Leu Ala
    130                 135                 140
```

<210> SEQ ID NO 31
<211> LENGTH: 433
<212> TYPE: DNA
<213> ORGANISM: Artificial Sequence
<220> FEATURE:
<223> OTHER INFORMATION: chemically synthesized

<400> SEQUENCE: 31

```
atgaaatgca gctgggtttt cctcttcctc ctgtcagtaa ttgcaggtgt ccaatcccag    60
gttcaactgc agcagtctgg gtctgagctg gtgaggcctg ggcttcagt gacgctgtcc    120 tgcaaggctt cgggctacac atttactgac tatgaaatgc actgggtgaa gcagacacct   180
gtgcatggcc tggaatggat tggagcgatt gatcctgaaa ctggtaaaac tgcctacaat   240
cagaagttca aggcaagac cacactgact gcagacaaat ccccagcac agcctacatg     300 gagttccgca gcctgacatc tgaggactct gccgtccatt actgtacaag agagttgact   360
tactggggcc aagggactct ggtcactgtc tctgcagcca aaacgacacc cccatcggtc   420
ttccccctgg cac                                                      433
```

<210> SEQ ID NO 32
<211> LENGTH: 144
<212> TYPE: PRT
<213> ORGANISM: Artificial Sequence
<220> FEATURE:
<223> OTHER INFORMATION: chemically synthesized

<400> SEQUENCE: 32

```
Met Lys Cys Ser Trp Val Phe Leu Phe Leu Leu Ser Val Ile Ala Gly
1               5                   10                  15

Val Gln Ser Gln Val Gln Leu Gln Gln Ser Gly Ser Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Lys Thr Ala Tyr Asn
65                  70                  75                  80

Gln Lys Phe Lys Gly Lys Thr Thr Leu Thr Ala Asp Lys Ser Pro Ser
                85                  90                  95

Thr Ala Tyr Met Glu Phe Arg Ser Leu Thr Ser Glu Asp Ser Ala Val
            100                 105                 110

His Tyr Cys Thr Arg Glu Leu Thr Tyr Trp Gly Gln Gly Thr Leu Val
        115                 120                 125

Thr Val Ser Ala Ala Lys Thr Thr Pro Pro Ser Val Phe Pro Leu Ala
    130                 135                 140
```

<210> SEQ ID NO 33
<211> LENGTH: 446
<212> TYPE: DNA
<213> ORGANISM: Artificial Sequence
<220> FEATURE:
<223> OTHER INFORMATION: chemically synthesized

<400> SEQUENCE: 33

```
atgaaatgca gctgggtttt cctcttcctc ctgtcagtaa ttgcaggtgt ccaatcccag    60
gttcaactgc agcagtctgg gtctgagctg gtgaggcctg ggcttcagt gacgctgtcc   120
tgcaaggctt cgggctacac atttactgac tatgaaatgc actgggtgaa gcagacacct   180
gtgcatggcc tggaatggat tggagcgatt gatcctgaaa ctggtaaaac tgcctacaat   240
cagaagttca gggcaagac cacactgact gcagacaaat cctccagcac agcctacatg   300
gagttccgca gcctgacatc tgaggactct gccgtccatt actgcacaag agagttgact   360
tactggggcc aagggactct ggtcactgtc tctgcagcca aaacgacacc cccaccegtc   420
tatccattgg cccctggaag cttggg                                       446
```

<210> SEQ ID NO 34
<211> LENGTH: 148
<212> TYPE: PRT
<213> ORGANISM: Artificial Sequence
<220> FEATURE:
<223> OTHER INFORMATION: chemically synthesized

<400> SEQUENCE: 34

```
Met Lys Cys Ser Trp Val Phe Leu Phe Leu Leu Ser Val Ile Ala Gly
1               5                   10                  15

Val Gln Ser Gln Val Gln Leu Gln Gln Ser Gly Ser Glu Leu Val Arg
            20                  25                  30

Pro Gly Ala Ser Val Thr Leu Ser Cys Lys Ala Ser Gly Tyr Thr Phe
        35                  40                  45
```

```
Thr Asp Tyr Glu Met His Trp Val Lys Gln Thr Pro Val His Gly Leu
         50                  55                  60

Glu Trp Ile Gly Ala Ile Asp Pro Glu Thr Gly Lys Thr Ala Tyr Asn
 65                  70                  75                  80

Gln Lys Phe Lys Gly Lys Thr Thr Leu Thr Ala Asp Lys Ser Ser Ser
             85                  90                  95

Thr Ala Tyr Met Glu Phe Arg Ser Leu Thr Ser Glu Asp Ser Ala Val
             100                 105                 110

His Tyr Cys Thr Arg Glu Leu Thr Tyr Trp Gly Gln Gly Thr Leu Val
         115                 120                 125

Thr Val Ser Ala Ala Lys Thr Thr Pro Pro Val Tyr Pro Leu Ala
130                 135                 140

Pro Gly Ser Leu
145
```

<210> SEQ ID NO 35
<211> LENGTH: 446
<212> TYPE: DNA
<213> ORGANISM: Artificial Sequence
<220> FEATURE:
<223> OTHER INFORMATION: chemically synthesized

<400> SEQUENCE: 35

```
atgaaatgga cctgggtttt tctcttcctc ctgtcagtaa ttgcaggtgt ccaatcccag    60
gttcaactgc agcagtctgg gtctgagctg gtgaggcctg gggcttcagt gacgctgtcc   120
tgcaaggctt cgggctacac atttactgac atgaaatgca ctgggtgaa gcagacacct    180
gtgcatggcc tggaatggat tggagcgatt gatcctgaaa ctggtaaaac tgcctacaat   240
cagaagttca gggcaagac cacactgact gcagacaaat cctccagcac agcctacatg   300
gagttccgca gcctgacatc tgaggactct gccgtccatt actgtacaag agagttgact   360
tactggggcc aagggactct ggtcactgtc tctgcagcca aaacgacacc cccacccgtc   420
tatcccctgg cccctggaag cttggg                                        446
```

<210> SEQ ID NO 36
<211> LENGTH: 148
<212> TYPE: PRT
<213> ORGANISM: Artificial Sequence
<220> FEATURE:
<223> OTHER INFORMATION: chemically synthesized

<400> SEQUENCE: 36

```
Met Lys Trp Thr Trp Val Phe Leu Phe Leu Leu Ser Val Ile Ala Gly
 1               5                   10                  15

Val Gln Ser Gln Val Gln Leu Gln Gln Ser Gly Ser Glu Leu Val Arg
             20                  25                  30

Pro Gly Ala Ser Val Thr Leu Ser Cys Lys Ala Ser Gly Tyr Thr Phe
         35                  40                  45

Thr Asp Tyr Glu Met His Trp Val Lys Gln Thr Pro Val His Gly Leu
     50                  55                  60

Glu Trp Ile Gly Ala Ile Asp Pro Glu Thr Gly Lys Thr Ala Tyr Asn
 65                  70                  75                  80

Gln Lys Phe Lys Gly Lys Thr Thr Leu Thr Ala Asp Lys Ser Ser Ser
             85                  90                  95

Thr Ala Tyr Met Glu Phe Arg Ser Leu Thr Ser Glu Asp Ser Ala Val
             100                 105                 110

His Tyr Cys Thr Arg Glu Leu Thr Tyr Trp Gly Gln Gly Thr Leu Val
```

```
                115                 120                 125
Thr Val Ser Ala Ala Lys Thr Thr Pro Pro Val Tyr Pro Leu Ala
    130                 135                 140

Pro Gly Ser Leu
145

<210> SEQ ID NO 37
<211> LENGTH: 447
<212> TYPE: DNA
<213> ORGANISM: Artificial Sequence
<220> FEATURE:
<223> OTHER INFORMATION: chemically synthesized

<400> SEQUENCE: 37
atggaatgga gctgggtttt cctcttcctc ctgtcagtaa ttgcaggtgt ccaatcccag     60
gttcaactgc agcagtctgg gtctgagctg gtgaggcctg ggcttcagt gacgctgtcc    120 tgcaaggctt cgggctacac atttactgac tatgaaatgc actgggtgaa gcagacacct    180
gtgcatggcc tggaatggat aggagcgatt gatcctgaaa ctggtaaaac tgcctacaat    240
cagaagttca gggcaagac cacactgact gcagacaaat cctccagcac agcctacatg    300
gagttccgca gcctgacatc tgaggactct gccgtccatt actgtacaag agagttgact    360
tactggggcc aagggactct ggtcactgtc tctgcagcca aaacgacacc cccacccgtc    420
tatccattgg ccccctggaa gcttggg                                        447

<210> SEQ ID NO 38
<211> LENGTH: 149
<212> TYPE: PRT
<213> ORGANISM: Artificial Sequence
<220> FEATURE:
<223> OTHER INFORMATION: chemically synthesized

<400> SEQUENCE: 38

Met Glu Trp Ser Trp Val Phe Leu Phe Leu Leu Ser Val Ile Ala Gly
1               5                   10                  15

Val Gln Ser Gln Val Gln Leu Gln Gln Ser Gly Ser Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Lys Thr Ala Tyr Asn
65                  70                  75                  80

Gln Lys Phe Lys Gly Lys Thr Thr Leu Thr Ala Asp Lys Ser Ser Ser
                85                  90                  95

Thr Ala Tyr Met Glu Phe Arg Ser Leu Thr Ser Glu Asp Ser Ala Val
            100                 105                 110

His Tyr Cys Thr Arg Glu Leu Thr Tyr Trp Gly Gln Gly Thr Leu Val
        115                 120                 125

Thr Val Ser Ala Ala Lys Thr Thr Pro Pro Val Tyr Pro Leu Ala
    130                 135                 140

Pro Trp Lys Leu Gly
145

<210> SEQ ID NO 39
<211> LENGTH: 145
<212> TYPE: PRT
<213> ORGANISM: Artificial Sequence
<220> FEATURE:
```

<223> OTHER INFORMATION: chemically synthesized

<400> SEQUENCE: 39

Met Lys Cys Ser Trp Val Phe Leu Phe Leu Leu Ser Val Ile Ala Gly
1               5                   10                  15

Val Gln Ser Gln Val Gln Leu Gln Gln Ser Gly Ser Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Lys Thr Ala Tyr Asn
65                  70                  75                  80

Gln Lys Phe Lys Gly Lys Thr Thr Leu Thr Ala Asp Lys Ser Ser Ser
                85                  90                  95

Thr Ala Tyr Met Glu Phe Arg Ser Leu Thr Ser Glu Asp Ser Ala Val
            100                 105                 110

His Tyr Cys Thr Arg Glu Leu Thr Tyr Trp Gly Gln Gly Thr Leu Val
        115                 120                 125

Thr Val Ser Ala Ala Lys Thr Thr Pro Pro Ser Val Phe Pro Leu Ala
    130                 135                 140

Pro
145

<210> SEQ ID NO 40
<211> LENGTH: 8
<212> TYPE: PRT
<213> ORGANISM: Artificial Sequence
<220> FEATURE:
<223> OTHER INFORMATION: chemically synthesized

<400> SEQUENCE: 40

Ile Asp Pro Glu Thr Gly Lys Thr
1               5

<210> SEQ ID NO 41
<211> LENGTH: 6
<212> TYPE: PRT
<213> ORGANISM: Artificial Sequence
<220> FEATURE:
<223> OTHER INFORMATION: chemically synthesized

<400> SEQUENCE: 41

Thr Arg Glu Leu Thr Tyr
1               5

<210> SEQ ID NO 42
<211> LENGTH: 499
<212> TYPE: DNA
<213> ORGANISM: Artificial Sequence
<220> FEATURE:
<223> OTHER INFORMATION: chemically synthesized

<400> SEQUENCE: 42
atgaagttgc ctgttaggct gttggtgctg atgttctgga ttcccgcctc ctcctccgac      60
gtgctgatga cccagacccc cctgaccctg tccgtgacca tcggccagcc tgcctccgtg     120
tcctgccggt cctcccagtc cctgctgttc tccaacggca agacctacct gaactggctg     180
ttccagcggc ctggccagtc ccccaagcgg ctgatctacc tggtgtccaa gctgaactcc     240
ggcgtgcccg accggtttac aggcaccggc tctggcaccg acttcagcct gaagatcagc     300

```
cgggtggaag ccgaggacct gggcgtgtac tactgcgtgc agggcaccca cttcccttgg    360
accttcggcg gaggcaccaa gctggaaatc aagcgggccg atgccgcccc taccgtgtcc    420
atcttcccac cctccagcga gcagctgacc tctggcggcg cttccgtcgt gtgcttcctg    480
aacaacttct accccaaag                                                  499
```

<210> SEQ ID NO 43
<211> LENGTH: 166
<212> TYPE: PRT
<213> ORGANISM: Artificial Sequence
<220> FEATURE:
<223> OTHER INFORMATION: chemically synthesized

<400> SEQUENCE: 43

```
Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Thr Leu Ser Val
            20                  25                  30

Thr Ile Gly Gln Pro Ala Ser Val Ser Cys Arg Ser Ser Gln Ser Leu
        35                  40                  45

Leu Phe Ser Asn Gly Lys Thr Tyr Leu Asn Trp Leu Phe Gln Arg Pro
    50                  55                  60

Gly Gln Ser Pro Lys Arg Leu Ile Tyr Leu Val Ser Lys Leu Asn Ser
65                  70                  75                  80

Gly Val Pro Asp Arg Phe Thr Gly Thr Gly Ser Gly Thr Asp Phe Ser
                85                  90                  95

Leu Lys Ile Ser Arg Val Glu Ala Glu Asp Leu Gly Val Tyr Tyr Cys
            100                 105                 110

Val Gln Gly Thr His Phe Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165
```

<210> SEQ ID NO 44
<211> LENGTH: 500
<212> TYPE: DNA
<213> ORGANISM: Artificial Sequence
<220> FEATURE:
<223> OTHER INFORMATION: chemically synthesized

<400> SEQUENCE: 44

```
atgaagttgc ctgttaggct gttggtgctg atgttctgga ttccgcctc ctcctccgac     60 gtgctgatga cccagacccc cctgaccctg tccgtgacca tcggccagcc tgcctctgtg   120
tcctgccggt cctcccagtc cctgctgttc tccaacggca gacctacct gaactggctg    180 ttccagcggc ctggccagtc ccccaagcgg ctgatctacc tggtgtccaa gctgaactcc   240
ggcgtgcccg accggtttac aggcaccggc tctggcaccg acttcagcct gaagatcagc   300
cgggtggaag ccgaggacct gggcgtgtac tactgcgtgc agggcaccca cttcccttgg   360
accttcggcg gaggcaccaa gctggaaatc aagcgggccg atgccgcccc taccgtgtcc   420
atcttcccac cctccagcga gcagctgacc tctggcggcg cttccgtcgt gtgcttcctg   480
aacaacttct accccagaga                                                500
```

<210> SEQ ID NO 45
<211> LENGTH: 166
<212> TYPE: PRT
<213> ORGANISM: Artificial Sequence
<220> FEATURE:
<223> OTHER INFORMATION: chemically synthesized

<400> SEQUENCE: 45

```
Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Thr Leu Ser Val
            20                  25                  30

Thr Ile Gly Gln Pro Ala Ser Val Ser Cys Arg Ser Ser Gln Ser Leu
        35                  40                  45

Leu Phe Ser Asn Gly Lys Thr Tyr Leu Asn Trp Leu Phe Gln Arg Pro
    50                  55                  60

Gly Gln Ser Pro Lys Arg Leu Ile Tyr Leu Val Ser Lys Leu Asn Ser
65                  70                  75                  80

Gly Val Pro Asp Arg Phe Thr Gly Thr Gly Ser Gly Thr Asp Phe Ser
                85                  90                  95

Leu Lys Ile Ser Arg Val Glu Ala Glu Asp Leu Gly Val Tyr Tyr Cys
            100                 105                 110

Val Gln Gly Thr His Phe Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg
                165
```

<210> SEQ ID NO 46
<211> LENGTH: 499
<212> TYPE: DNA
<213> ORGANISM: Artificial Sequence
<220> FEATURE:
<223> OTHER INFORMATION: chemically synthesized

<400> SEQUENCE: 46

```
atgaagttgc ctgtaggctg ttggtgctga tgttctggat tcccgcctcc tcctccgacg    60
tgcagatgac ccagaccccc ctgaccctgt ccgtgaccat cggccagcct gcctctgtgt   120
cctgccggtc ctcccagtcc ctgctgttct ccaacggcaa gacctacctg aactggctgt   180
tccagcggcc tggccagtcc cccaagcggc tgatctacct ggtgtccaag ctgaactccg   240
gcgtgcccga ccgvtttaca ggcaccggct ctggcaccga cttcagcctg aagatcagcc   300
gggtggaagc cgaggacctg ggcgtgtact actgcgtgca gggcacccac ttcccttgga   360
ccttcggcgg aggcaccaag ctggaaatca gcgggccga tgccgcccct accgtgtcca   420
tcttcccacc ctccagcgag cagctgacct ctggcggcgc ttccgtcgtg tgcttcctga   480
acaacttcta ccccagaga                                                499
```

<210> SEQ ID NO 47
<211> LENGTH: 165
<212> TYPE: PRT
<213> ORGANISM: Artificial Sequence
<220> FEATURE:
<223> OTHER INFORMATION: chemically synthesized

<400> SEQUENCE: 47

Glu Val Ala Cys Arg Leu Leu Val Leu Met Phe Trp Ile Pro Ala Ser
1               5                   10                  15

Ser Ser Asp Val Gln Met Thr Gln Thr Pro Leu Thr Leu Ser Val Thr
            20                  25                  30

Ile Gly Gln Pro Ala Ser Val Ser Cys Arg Ser Ser Gln Ser Leu Leu
                35                  40                  45

Phe Ser Asn Gly Lys Thr Tyr Leu Asn Trp Leu Phe Gln Arg Pro Gly
        50                  55                  60

Gln Ser Pro Lys Arg Leu Ile Tyr Leu Val Ser Lys Leu Asn Ser Gly
65                  70                  75                  80

Val Pro Asp Arg Phe Thr Gly Thr Gly Ser Gly Thr Asp Phe Ser Leu
                85                  90                  95

Lys Ile Ser Arg Val Glu Ala Glu Asp Leu Gly Val Tyr Tyr Cys Val
                100                 105                 110

Gln Gly Thr His Phe Pro Trp Thr Phe Gly Gly Gly Thr Lys Leu Glu
            115                 120                 125

Ile Lys Arg Ala Asp Ala Ala Pro Thr Val Ser Ile Phe Pro Pro Ser
        130                 135                 140

Ser Glu Gln Leu Thr Ser Gly Gly Ala Ser Val Val Cys Phe Leu Asn
145                 150                 155                 160

Asn Phe Tyr Pro Arg
            165

<210> SEQ ID NO 48
<211> LENGTH: 500
<212> TYPE: DNA
<213> ORGANISM: Artificial Sequence
<220> FEATURE:
<223> OTHER INFORMATION: chemically synthesized

<400> SEQUENCE: 48
atgaagttgc ctgttaggct gttggtgctg atgttctgga ttcccgcctc ctcctccgac    60
gtgctgatga cccagacccc cctgaccctg tccgtgacca tcggccagcc tgcctctgtg   120
tcctgccggt cctcccagtc cctgctgttc tccaacggca agacctacct gaactggctg   180
ttccagcggc ctggccagtc ccccaagcgg ctgatctacc tggtgtccaa gctgaactcc   240
ggcgtgcccg accggtttac aggcaccggc tctggcaccg acttcagcct gaagatcagc   300
cgggtggaag ccgaggacct gggcgtgtac tactgcgtgc agggcaccca cttcccttgg   360
accttcggcg gaggcaccaa gctggaaatc aagcgggccg atgccgcccc taccgtgtcc   420
atcttcccac cctccagcga gcagctgacc tctggcggcg cttccgtcgt gtgcttcctg   480
aacaacttct accccaaaga                                              500

<210> SEQ ID NO 49
<211> LENGTH: 166
<212> TYPE: PRT
<213> ORGANISM: Artificial Sequence
<220> FEATURE:
<223> OTHER INFORMATION: chemically synthesized

<400> SEQUENCE: 49

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Thr Leu Ser Val
            20                  25                  30

Thr Ile Gly Gln Pro Ala Ser Val Ser Cys Arg Ser Ser Gln Ser Leu
        35                  40                  45

Leu Phe Ser Asn Gly Lys Thr Tyr Leu Asn Trp Leu Phe Gln Arg Pro
            50                  55                  60

Gly Gln Ser Pro Lys Arg Leu Ile Tyr Leu Val Ser Lys Leu Asn Ser
 65                  70                  75                  80

Gly Val Pro Asp Arg Phe Thr Gly Thr Gly Ser Gly Thr Asp Phe Ser
                    85                  90                  95

Leu Lys Ile Ser Arg Val Glu Ala Glu Asp Leu Gly Val Tyr Tyr Cys
                100                 105                 110

Val Gln Gly Thr His Phe Pro Trp Thr Phe Gly Gly Gly Thr Lys Leu
            115                 120                 125

Glu Ile Lys Arg Ala Asp Ala Ala Pro Thr Val Ser Ile Phe Pro Pro
        130                 135                 140

Ser Ser Glu Gln Leu Thr Ser Gly Gly Ala Ser Val Val Cys Phe Leu
145                 150                 155                 160

Asn Asn Phe Tyr Pro Arg
                165

<210> SEQ ID NO 50
<211> LENGTH: 446
<212> TYPE: DNA
<213> ORGANISM: Artificial Sequence
<220> FEATURE:
<223> OTHER INFORMATION: chemically synthesized

<400> SEQUENCE: 50
atggaatgca cctgggttct tctcttcctc ctgtcagtaa ttgcaggtgt ccaatcccag    60
gttcatctgc agcagtctgg ggctgagctg gtgaggcctg ggcttcagt gacgctgccc    120 tgcaaggctt cgggctacac atttactgac tatgaaatgc actgggtgaa acagacacct   180
gtgcatggcc tggaatggat tggcgctatt gatcctgaaa ctggtgctat tgtctacgat   240
cagaagttca gggcaaggc cacactgact gcagacaaat cctccaacac agcctacatg    300
gagctccgca gcctgacatc tgaggactct gccgtctatt actgtacaag agagtttact   360
tactggggcc aagggactct ggtcactgtc tctgcagcca aaacgacacc cccacccgtc   420 tatccctgg ccctggaag cttggg                                         446

<210> SEQ ID NO 51
<211> LENGTH: 148
<212> TYPE: PRT
<213> ORGANISM: Artificial Sequence
<220> FEATURE:
<223> OTHER INFORMATION: chemically synthesized

<400> SEQUENCE: 51

Met Glu Cys Thr Trp Val Leu Leu Phe Leu Leu Ser Val Ile Ala Gly
 1                5                  10                  15

Val Gln Ser Gln Val His Leu Gln Gln Ser Gly Ala Glu Leu Val Arg
             20                  25                  30

Pro Gly Ala Ser Val Thr Leu Pro Cys Lys Ala Ser Gly Tyr Thr Phe
         35                  40                  45

Thr Asp Tyr Glu Met His Trp Val Lys Gln Thr Pro Val His Gly Leu
     50                  55                  60

Glu Trp Ile Gly Ala Ile Asp Pro Glu Thr Gly Ala Ile Val Tyr Asp
 65                  70                  75                  80

Gln Lys Phe Lys Gly Lys Ala Thr Leu Thr Ala Asp Lys Ser Ser Asn
                 85                  90                  95

Thr Ala Tyr Met Glu Leu Arg Ser Leu Thr Ser Glu Asp Ser Ala Val
            100                 105                 110

Tyr Tyr Cys Thr Arg Glu Phe Thr Tyr Trp Gly Gln Gly Thr Leu Val
            115                 120                 125

Thr Val Ser Ala Ala Lys Thr Thr Pro Pro Val Tyr Pro Leu Ala
    130                 135                 140

Pro Gly Ser Leu
145

<210> SEQ ID NO 52
<211> LENGTH: 446
<212> TYPE: DNA
<213> ORGANISM: Artificial Sequence
<220> FEATURE:
<223> OTHER INFORMATION: chemically synthesized

<400> SEQUENCE: 52
atgggatgga gcgtggttta tctcttcctc ctgtcagtaa ttgcaggtgt ccaatcccag      60
gttcatctgc agcagtctgg ggctgagctg gtgaggcctg gggcttcagt gacgctgccc     120
tgcaaggctt cgggctacac atttactgac tatgaaatgc actgggtgaa acagacacct     180
gtgcatggcc tggaatggat tggcgctatt gatcctgaaa ctggtgctat tgtctacaat     240
cagaagttca gggcaaggc cacactgact gcagacaaat cctccaacac agcctacatg      300
gagctccgca gcctgacatc tgaggactct gccgtctatt actgtacaag agagtttact     360
tactggggcc aagggactct ggtcactgtc tctgcagcca aaacgacacc cccatccgtt     420
tatcccctgg tccctggaag cttggg                                           446

<210> SEQ ID NO 53
<211> LENGTH: 148
<212> TYPE: PRT
<213> ORGANISM: Artificial Sequence
<220> FEATURE:
<223> OTHER INFORMATION: chemically synthesized

<400> SEQUENCE: 53

Met Gly Trp Ser Val Val Tyr Leu Phe Leu Leu Ser Val Ile Ala Gly
1               5                   10                  15

Val Gln Ser Gln Val His Leu Gln Gln Ser Gly Ala Glu Leu Val Arg
            20                  25                  30

Pro Gly Ala Ser Val Thr Leu Pro Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Ala Ile Val Tyr Asn
65                  70                  75                  80

Gln Lys Phe Lys Gly Lys Ala Thr Leu Thr Ala Asp Lys Ser Ser Asn
                85                  90                  95

Thr Ala Tyr Met Glu Leu Arg Ser Leu Thr Ser Glu Asp Ser Ala Val
            100                 105                 110

Tyr Tyr Cys Thr Arg Glu Phe Thr Tyr Trp Gly Gln Gly Thr Leu Val
        115                 120                 125

Thr Val Ser Ala Ala Lys Thr Thr Pro Ser Val Tyr Pro Leu Val
    130                 135                 140

Pro Gly Ser Leu
145

<210> SEQ ID NO 54
<211> LENGTH: 456
<212> TYPE: PRT

<213> ORGANISM: Artificial Sequence
<220> FEATURE:
<223> OTHER INFORMATION: chemically synthesized

<400> SEQUENCE: 54

```
Met Glu Cys Thr Trp Val Ile Leu Phe Leu Leu Ser Val Ile Ala Gly
1               5                   10                  15

Val Gln Ser Gln Val His Leu Gln Gln Ser Gly Ala Glu Leu Val Arg
            20                  25                  30

Pro Gly Ala Ser Val Thr Leu Pro Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Ala Ile Val Tyr Asn
65                  70                  75                  80

Gln Lys Phe Lys Gly Lys Ala Thr Leu Thr Ala Asp Lys Ser Ser Asn
                85                  90                  95

Thr Ala Tyr Met Glu Leu Arg Ser Leu Thr Ser Glu Asp Ser Ala Val
            100                 105                 110

Tyr Tyr Cys Thr Arg Glu Phe Thr Tyr Trp Gly Gln Gly Thr Leu Val
        115                 120                 125

Thr Val Ser Ala Ala Lys Thr Thr Pro Pro Ser Val Tyr Pro Leu Ala
130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Ser Val Thr Val Pro Ser Ser Pro Arg Pro
        195                 200                 205

Ser Glu Thr Val Thr Cys Asn Val Ala His Pro Ala Ser Ser Thr Lys
    210                 215                 220

Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
                245                 250                 255

Lys Asp Val Leu Thr Ile Thr Leu Thr Pro Lys Val Thr Cys Val Val
            260                 265                 270

Val Asp Ile Ser Lys Asp Asp Pro Glu Val Gln Phe Ser Trp Phe Val
        275                 280                 285

Asp Asp Val Glu Val His Thr Ala Gln Thr Gln Pro Arg Glu Glu Gln
    290                 295                 300

Phe Asn Ser Thr Phe Arg Ser Val Ser Glu Leu Pro Ile Met His Gln
305                 310                 315                 320

Asp Trp Leu Asn Gly Lys Glu Phe Lys Cys Arg Val Asn Ser Ala Ala
                325                 330                 335

Phe Pro Ala Pro Ile Glu Lys Thr Ile Ser Lys Thr Lys Gly Arg Pro
            340                 345                 350

Lys Ala Pro Gln Val Tyr Thr Ile Pro Pro Lys Glu Gln Met Ala
        355                 360                 365

Lys Asp Lys Val Ser Leu Thr Cys Met Ile Thr Asp Phe Phe Pro Glu
    370                 375                 380

Asp Ile Thr Val Glu Trp Gln Trp Asn Gly Gln Pro Ala Glu Asn Tyr
385                 390                 395                 400
```

-continued

Lys Asn Thr Gln Pro Ile Met Asn Thr Asn Gly Ser Tyr Phe Val Tyr
                405                 410                 415

Ser Lys Leu Asn Val Gln Lys Ser Asn Trp Glu Ala Gly Asn Thr Phe
            420                 425                 430

Thr Cys Ser Val Leu His Glu Gly Leu His Asn His Thr Glu Lys
        435                 440                 445

Ser Leu Ser His Ser Pro Gly Lys
    450                 455

<210> SEQ ID NO 55
<211> LENGTH: 238
<212> TYPE: PRT
<213> ORGANISM: Artificial Sequence
<220> FEATURE:
<223> OTHER INFORMATION: chemically synthesized

<400> SEQUENCE: 55

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Thr Leu Ser Val
            20                  25                  30

Thr Ile Gly Gln Pro Ala Ser Val Ser Cys Arg Ser Ser Gln Ser Leu
        35                  40                  45

Leu Phe Ser Asn Gly Lys Thr Tyr Leu Asn Trp Leu Phe Gln Arg Pro
    50                  55                  60

Gly Gln Ser Pro Lys Arg Leu Ile Tyr Leu Val Ser Lys Leu Asn Ser
65                  70                  75                  80

Gly Val Pro Asp Arg Phe Thr Gly Thr Gly Ser Gly Thr Asp Phe Ser
                85                  90                  95

Leu Lys Ile Ser Arg Val Glu Ala Glu Asp Leu Gly Val Tyr Tyr Cys
            100                 105                 110

Val Gln Gly Thr His Phe Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 56
<211> LENGTH: 17
<212> TYPE: PRT
<213> ORGANISM: Artificial Sequence
<220> FEATURE:
<223> OTHER INFORMATION: chemically synthesized

<400> SEQUENCE: 56

Ser Lys Gly Glu Glu Pro Arg Ala Gly Lys Glu Glu Ser Gly Val Ser
1               5                   10                  15

Cys

<210> SEQ ID NO 57
<211> LENGTH: 456
<212> TYPE: PRT
<213> ORGANISM: Artificial Sequence
<220> FEATURE:
<223> OTHER INFORMATION: chemically synthesized

<400> SEQUENCE: 57

Met Lys Cys Ser Trp Val Phe Leu Phe Leu Leu Ser Val Ile Ala Gly
1               5                   10                  15

Val Gln Ser Gln Val Gln Leu Gln Gln Ser Gly Ser Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Trp Ile Gly Ala Ile Asp Pro Glu Thr Gly Lys Thr Ala Tyr Asn
65                  70                  75                  80

Gln Lys Phe Lys Gly Lys Thr Thr Leu Thr Ala Asp Lys Ser Ser Ser
                85                  90                  95

Thr Ala Tyr Met Glu Phe Arg Ser Leu Thr Ser Glu Asp Ser Ala Val
            100                 105                 110

His Tyr Cys Thr Arg Glu Leu Thr Tyr Trp Gly Gln Gly Thr Leu Val
        115                 120                 125

Thr Val Ser Ala Ala Lys Thr Thr Pro Pro Ser Val Tyr Pro Leu Ala
    130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Ser Val Thr Val Pro Ser Ser Pro Arg Pro
        195                 200                 205

Ser Glu Thr Val Thr Cys Asn Val Ala His Pro Ala Ser Ser Thr Lys
    210                 215                 220

Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
                245                 250                 255

Lys Asp Val Leu Thr Ile Thr Leu Thr Pro Lys Val Thr Cys Val Val
            260                 265                 270

Val Asp Ile Ser Lys Asp Asp Pro Glu Val Gln Phe Ser Trp Phe Val
        275                 280                 285

Asp Asp Val Glu Val His Thr Ala Gln Thr Gln Pro Arg Glu Glu Gln
    290                 295                 300

Phe Asn Ser Thr Phe Arg Ser Val Ser Glu Leu Pro Ile Met His Gln
305                 310                 315                 320

Asp Trp Leu Asn Gly Lys Glu Phe Lys Cys Arg Val Asn Ser Ala Ala
                325                 330                 335

Phe Pro Ala Pro Ile Glu Lys Thr Ile Ser Lys Thr Lys Gly Arg Pro
            340                 345                 350

Lys Ala Pro Gln Val Tyr Thr Ile Pro Pro Pro Lys Glu Gln Met Ala

```
                355                 360                 365
Lys Asp Lys Val Ser Leu Thr Cys Met Ile Thr Asp Phe Phe Pro Glu
    370                 375                 380

Asp Ile Thr Val Glu Trp Gln Trp Asn Gly Gln Pro Ala Glu Asn Tyr
385                 390                 395                 400

Lys Asn Thr Gln Pro Ile Met Asn Thr Asn Gly Ser Tyr Phe Val Tyr
                405                 410                 415

Ser Lys Leu Asn Val Gln Lys Ser Asn Trp Glu Ala Gly Asn Thr Phe
            420                 425                 430

Thr Cys Ser Val Leu His Glu Gly Leu His Asn His His Thr Glu Lys
        435                 440                 445

Ser Leu Ser His Ser Pro Gly Lys
    450                 455

<210> SEQ ID NO 58
<211> LENGTH: 238
<212> TYPE: PRT
<213> ORGANISM: Artificial Sequence
<220> FEATURE:
<223> OTHER INFORMATION: chemically synthesized

<400> SEQUENCE: 58

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Thr Leu Ser Val
            20                  25                  30

Thr Ile Gly Gln Pro Ala Ser Val Ser Cys Arg Ser Ser Gln Ser Leu
        35                  40                  45

Leu Phe Ser Asn Gly Lys Thr Tyr Leu Asn Trp Leu Phe Gln Arg Pro
    50                  55                  60

Gly Gln Ser Pro Lys Arg Leu Ile Tyr Leu Val Ser Lys Leu Asn Ser
65                  70                  75                  80

Gly Val Pro Asp Arg Phe Thr Gly Thr Gly Ser Gly Thr Asp Phe Ser
                85                  90                  95

Leu Lys Ile Ser Arg Val Glu Ala Glu Asp Leu Gly Val Tyr Tyr Cys
            100                 105                 110

Val Gln Gly Thr His Phe Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 59
<211> LENGTH: 19
<212> TYPE: PRT
<213> ORGANISM: Artificial Sequence
```

```
<220> FEATURE:
<223> OTHER INFORMATION: chemically synthesized

<400> SEQUENCE: 59

Ser Lys Gly Glu Glu Pro Arg Ala Gly Lys Glu Glu Ser Gly Val Ser
1               5                   10                  15

Val Ser Cys
```

US 8,722,041 B2

ANTI-HUMAN EQUILIBRATIVE NUCLEOSIDE TRANSPORTER 1 (HENT1) ANTIBODIES AND METHODS OF USE THEREOF

RELATED APPLICATIONS

This application claims the benefit of U.S. Provisional Application No. 61/355,357, filed Jun. 16, 2010 and U.S. Provisional Application No. 61/432,702, filed Jan. 14, 2011. The contents of each of these applications are hereby incorporated by reference in their entirety.

FIELD OF THE INVENTION

This invention relates generally to the generation of monoclonal antibodies that recognize human Equilibrative Nucleoside Transporter 1 (hENT1), and to methods of using these monoclonal antibodies as therapeutics.

INCORPORATION-BY-REFERENCE OF SEQUENCE LISTING

The contents of the text file named "37269503USSeq.txt," which was created on Jun. 16, 2011 and is 61.0 KB in size, are hereby incorporated by reference in their entirety

BACKGROUND OF THE INVENTION

Human equilibrative nucleoside transporter 1 (hENT1) is a protein that is encoded by the SLC29A1 gene. This gene is a member of the equilibrative nucleoside transporter family. The gene encodes a transmembrane glycoprotein that localizes to the plasma and mitochondrial membranes and mediates the cellular uptake of nucleosides from the surrounding medium. The protein is categorized as an equilibrative (as opposed to concentrative) transporter that is sensitive to inhibition by nitrobenzylthioinosine (NBMPR). Nucleoside transporters are required for nucleotide synthesis in cells that lack de novo nucleoside synthesis pathways, and are also necessary for the uptake of cytotoxic nucleosides and nucleoside analogue drugs used for cancer and viral chemotherapies.

Accordingly, there exists a need for therapies that treat or otherwise ameliorate a disorder associated with aberrant hENT1 expression and/or activity.

SUMMARY OF THE INVENTION

The present invention provides monoclonal antibodies which specifically bind to human Equilibrative Nucleoside Transporter 1 (hENT1) or a biologically active fragment thereof. The hENT1 antibodies are useful in detecting patients or patient samples with low or otherwise reduced hENT1 expression and/or activity. For example, the hENT1 antibodies can be used to screen patients having cancers and other neoplastic disorders in which hENT1 expression and/or activity is low or otherwise reduced, such as, for example, acute myeloid leukemia (AML) or pancreatic cancer and other solid tumors. The hENT1 antibodies are useful to identify patients for treatment based on detected hENT1 expression and/or activity level. The hENT1 antibodies are useful as a prognosis tool for subjects diagnosed a disorder associated with low hENT1 expression and/or activity such as, for example, cancer or other neoplastic disorders. Prognosis of a disorder associated with low hENT1 expression and/or activity is also determined by measuring hENT1 expression and/or activity level over time, such as for example, during the course of therapeutic methods.

The hENT1 antibodies of the invention are useful as companion diagnostics for established cancer drugs such as nucleoside analogue drugs and/or drugs derived from nucleoside analogues. For example, the hENT1 antibodies are useful in conjunction with chemotherapy agents such as pyrimidine derivatives including, for example, cytarabine, gemcitabine, azacytidine, and derivatives thereof, and purine derivatives including, for example, fludarabine, cladribine, clofarabine and derivatives thereof.

Exemplary monoclonal antibodies of the invention include, for example, a variable heavy chain sequence such the VH3-12 variable heavy chain, the VH5-9 variable heavy chain, the VH5-12 variable heavy chain, the VH5-13 variable heavy chain, the VH5-3 variable heavy chain, the VH5-11 variable heavy chain, or the consensus variable heavy chain provided herein and referred to as the consensus variable heavy chain region sequence 1 (consensus VH sequence 1). Exemplary variable heavy chain sequences for the hENT1 antibodies of the invention also include the VH1-1 variable heavy chain, the VH1-4 variable heavy chain, the VH1-6 variable heavy chain, the VH4-2 variable heavy chain, the VH4-3 variable heavy chain, the VH4-4 variable heavy chain or the consensus variable heavy chain provided herein and referred to as the consensus variable heavy chain region sequence 2 (consensus VH sequence 2). Exemplary monoclonal antibodies of the invention include, for example, a light chain variable sequence such as, for example, the VL2 variable light chain, the VL10 variable light chain, the VL11 variable light chain, the VL20 variable light chain, the VL21 light chain, or the consensus variable light chain provided herein and referred to as the consensus variable light chain region sequence 1 (consensus VL sequence 1). Exemplary variable light chain sequences for the hENT1 antibodies of the invention also include the VL2-2 variable light chain, the VL2-3 variable light chain, the VL2-7 variable light chain, the VL2-10 variable light chain, the VL2-12 variable light chain, the VL2-16 variable light chain or the consensus variable light chain provided herein and referred to as the consensus variable light chain region sequence 2 (consensus VL sequence 2). These antibodies are respectively referred to herein as "hENT1 antibodies" or "anti-hENT1 antibodies". hENT1 antibodies include fully human monoclonal antibodies, as well as humanized monoclonal antibodies and chimeric antibodies. These antibodies show specificity for hENT1.

The hENT1 antibodies of the invention include a heavy chain variable region having the amino acid sequence of SEQ ID NOs: 2, 4, 6, 8, 9, 28, 30, 32, 34, 36, 38 or 39. The hENT1 antibodies of the invention include a light chain variable region having the amino acid sequence of SEQ ID NOs: 14, 16, 18, 20, 22, 23, 43, 45, 47 or 49.

Preferably, the variable heavy chains of the hENT1 antibodies of the invention include a variable heavy chain complementarity determining region 1 (VH CDR1) sequence comprising the amino acid sequence GYTFTDYE (SEQ ID NO: 10), a variable heavy chain complementarity determining region 2 (VH CDR2) sequence comprising the amino acid sequence IDPETGAI (SEQ ID NO: 11) or the amino acid sequence IDPETGKT (SEQ ID NO: 40), and a variable heavy chain complementarity determining region 3 (VH CDR3) sequence comprising the amino acid sequence TREFTY (SEQ ID NO: 12) or the amino acid sequence TRELTY (SEQ ID NO: 41).

The heavy chain variable regions of the hENT1 antibodies of the invention contain a variable heavy chain complementarity determining region 1 (VH CDR1) that includes an amino acid sequence at least 90%, 92%, 95%, 97% 98%, 99% or more identical to the amino acid sequence GYTFTDYE (SEQ ID NO: 10); a variable heavy chain complementarity determining region 2 (VH CDR2) that includes an amino acid sequence at least 90%, 92%, 95%, 97% 98%, 99% or more identical to the amino acid sequence IDPETGAI (SEQ ID NO: 11) or the amino acid sequence IDPETGKT (SEQ ID NO: 40); and a variable heavy chain complementarity determining region 3 (VH CDR3) that includes an amino acid sequence at least 90%, 92%, 95%, 97% 98%, 99% or more identical to the amino acid sequence TREFTY (SEQ ID NO: 12) or the amino acid sequence TRELTY (SEQ ID NO: 41).

The present invention provides methods of detecting hENT1 activity and/or expression in a patient or patient sample. The invention provides uses of the hENT1 antibodies in conjunction with established chemotherapies including, for example, nucleoside analogue drugs and/or drugs derived from nucleoside analogues. For example, the hENT1 antibodies are used in conjunction with chemotherapy agents such as pyrimidine derivatives including, for example, cytarabine, gemcitabine, azacytidine, and derivatives thereof, and purine derivatives including, for example, fludarabine, cladribine, clofarabine and derivatives thereof. Other suitable agents for use in combination with the hENT1 antibodies disclosed herein include antiviral agents such as, for example, ribavirin, and anticancer nucleoside agents such as 5-fluorouridine, which are substrates of nucleoside transporters. Thus, the hENT1 antibodies are also useful in conjunction with antiviral therapies, anticancer therapies and derivatives thereof.

The present invention also provides methods of treating or preventing pathologies associated with aberrant hENT1 expression and/or activity, or alleviating a symptom associated with such pathologies, by administering a monoclonal antibody of the invention to a subject in which such treatment or prevention is desired. The terms "patient" and "subject" are used interchangeably herein and throughout this description. The subject to be treated is, e.g., human. The monoclonal antibody is administered in an amount sufficient to treat, prevent or alleviate a symptom associated with the pathology. The amount of monoclonal antibody sufficient to treat or prevent the pathology in the subject is, for example, an amount that is sufficient to reduce hENT1 expression and/or activity.

The antibodies of the invention are capable of modulating, e.g., blocking, inhibiting, reducing, antagonizing, neutralizing or otherwise interfering with expression of hENT1 and/or one or more biological activities of hENT1. For example, the hENT1 antibodies completely or partially inhibit hENT1 expression and/or biological activity by partially or completely modulating, blocking, inhibiting, reducing antagonizing, neutralizing, or otherwise interfering with the expression and/or activity of hENT1, or otherwise partially or completely modulating, blocking, inhibiting, reducing, antagonizing, neutralizing hENT1 expression and/or activity. The hENT1 antibodies are considered to completely modulate, block, inhibit, reduce, antagonize, neutralize or otherwise interfere with hENT1 expression and/or biological activity when the level of hENT1 expression and/or activity in the presence of the hENT1 antibody is decreased by at least 95%, e.g., by 96%, 97%, 98%, 99% or 100% as compared to the level of hENT1 expression and/or activity in the absence of binding with an hENT1 antibody described herein. The hENT1 antibodies are considered to partially modulate, block, inhibit, reduce, antagonize, neutralize or otherwise interfere with hENT1 expression and/or activity when the level of hENT1 expression and/or activity in the presence of the hENT1 antibody is decreased by less than 95%, e.g., 10%, 20%, 25%, 30%, 40%, 50%, 60%, 75%, 80%, 85% or 90% as compared to the level of hENT1 expression and/or activity in the absence of binding with an hENT1 antibody described herein.

As used herein, the term "reduced" refers to a decreased expression and/or activity of hENT1 in the presence of a monoclonal antibody of the invention. hENT1 expression is decreased when the level of hENT1 expression in the presence of a monoclonal antibody of the invention is greater than or equal to 5%, 10%, 20%, 25%, 30%, 40%, 50%, 60%, 70%, 75%, 80%, 90%, 95%, 99%, or 100% lower than a control level of hENT1 expression. hENT1 expression level is determined using a variety of assays, including those described in the Examples provided herein. hENT1 activity is decreased when the level of one or more biological activities of hENT1 in the presence of a monoclonal antibody of the invention is greater than or equal to 5%, 10%, 20%, 25%, 30%, 40%, 50%, 60%, 70%, 75%, 80%, 90%, 95%, 99%, or 100% lower than a control level of hENT1 activity. hENT1 activity level is determined using a variety of assays.

Pathologies treated, ameliorated and/or prevented using the monoclonal antibodies of the invention (e.g., monoclonal antibodies) include, for example, cancer and other neoplastic indications such as AML and pancreatic cancer. Pathologies treated, ameliorated and/or prevented using the monoclonal antibodies of the invention (e.g., monoclonal antibodies) include, for example, viral indications such as hepatitis C, infectious diseases such as malaria, and blood diseases such as beta-thalassemia.

Pharmaceutical compositions according to the invention can include an antibody of the invention and a carrier. These pharmaceutical compositions can be included in kits, such as, for example, diagnostic kits.

DETAILED DESCRIPTION

Figure 1:
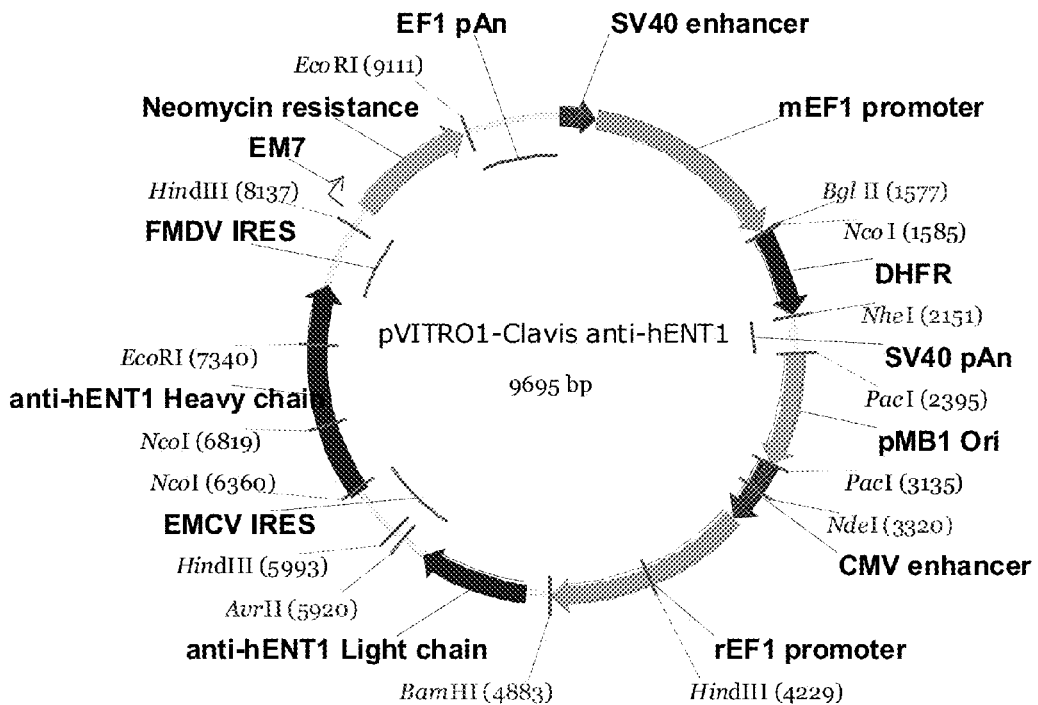
FIG. 1 is a schematic representation of the expression vector used to express the anti-hENT1 antibodies.

The present invention provides monoclonal antibodies that specifically bind hENT1. The antibodies of the present invention bind to an hENT1 epitope with an equilibrium binding constant ($K_d$) of ≤μM, e.g., ≤100 nM, preferably ≤10 nM, and more preferably 1 nM. For example, the hENT1 antibodies provided herein exhibit a $K_d$ in the range approximately between ≤1 nM to about 1 pM.

Nucleoside analogue drugs depend on nucleoside transporters to enter the cells where they exert their effect—these molecules do not cross the plasma membrane by diffusion, and efficient cellular uptake requires the presence of these specialized plasma membrane nucleoside transporter proteins.

Cytarabine and gemcitabine (Gemzar, Eli Lilly, Indianapolis, Ind.) are two anticancer drugs that depend on human Equilibrative Nucleoside Transporter 1 (hENT1) for their effect. A considerable proportion of cancer cells have low expression of hENT1. Low expression and/or activity of hENT1 has been found in patients having cancers and other neoplastic disorders such as, for example, acute myeloid leukemia (AML) or pancreatic cancer. Low clinical effect of treatment has been correlated with reduced or no presence of hENT1 in the cancer cells. (See e.g., Galmarini, et al., "Potential mechanisms of resistance to cytarabine in AML patients," Leuk Res 26 (2002) 621-629; Farrell, et al., "Human Equilibrative Nucleoside Transporter 1 Levels Predict Response to Gemcitabine in Patients With Pancreatic Cancer," Gastroenterology 136 (2009) 187-195; and Giovannetti, et al., "Transcription analysis of human equilibrative nucleoside transporter-1 predicts survival in pancreas cancer patients treated with gemcitabine," Cancer Res 66 (2006) 3928-3935). Studies have shown a direct correlation between the lack of hENT1 expression on a pancreatic cancer patient's tumor cells and that patient's poor response to nucleoside analogue and other chemotherapeutic drugs such as gemcitabine. (See Farrell, et al., "Human Equilibrative Nucleoside Transporter 1 Levels Predict Response to Gemcitabine in Patients With Pancreatic Cancer," Gastroenterology 136 (2009) 187-195). hENT1 is also important for the oral uptake of ribavirin and can cause resistance to ribavirin hepatitis C treatment. (See Ibarra et al., "Reduced ribavirin antiviral efficacy via nucleoside transporter-mediated drug resistance," J. Virol., vol. 83(9): 4583-47 (2009)).

Thus, the hENT1 antibodies of the invention are useful in detecting hENT1 levels in a patient or patient sample. The hENT1 antibodies of the invention are useful as companion diagnostics for current cancer drugs or antiviral drugs. For example, the hENT1 antibodies are useful in conjunction with chemotherapy agents such as nucleoside analogue drugs including cytarabine, azacytidine gemcitabine, gemcitabine-5'-elaidic acid ester, cytarabine-5'-elaidic acid ester, 5-azacytidine-5'-elaidic acid ester and ribavirin-5'-elaidic acid ester. The hENT1 antibodies are also useful in combinational with agents such as purine and pyrimidine nucleoside derivatives. (See Quashie et al., "Uptake of purines in *Plasmodium falciparum*-infected human erythrocytes is mostly mediated by the human equilibrative nucleoside transporter and the human facilitative nucleobase transporter," Malaria Journal, vol. 9: 36 (2010)).

The hENT1 antibodies of the invention are useful to identify a population of patients with low or otherwise reduced hENT1 expression and/or activity for additional or otherwise altered treatment regimens. For example, this identified patient population is administered a treatment that is designed to allow uptake in hENT1 deficient cells, such as for example, gemcitabine-5'-elaidic acid ester or gemcitabine-N4-elaidic acid amide, cytarabine-5'-elaidic acid ester, or 5-azacytidine-5'-elaidic acid ester or ribavirin-5'-elaidic acid ester. (See Brueckner, et al., "Delivery of 5-azacytidine to human cancer cells by elaidic acid esterification increases therapeutic drug efficacy," Mol Cancer Ther., vol. 9(5): 1256-1264 (2010)). Studies have shown that these drugs, in contrast to established nucleoside drugs such as gemcitabine, cytarabine and azacytidine, are able to enter cancer cells and retain their activity in cancer cells independent of the hENT1 expression level in the cancer cell. (See e.g. Breistol, et al., "Antitumor activity of P-4055 (elaidic acid-cytarabine) compared to cytarabine in metastatic and s.c. human tumor xenograft models," Cancer Res 59 (1999) 2944-2949; and Galmarini et al., "CP-4055 and CP-4126 are active in ara-C and gemcitabine-resistant lymphoma cell lines," Br J Haematol 144 (2009) 273-275).

The uptake of gemcitabine-5'-elaidic acid ester and cytarabine-5'-elaidic acid ester in hENT1 deficient cells has been confirmed also in vitro with confirmed high formation of the active triphosphate metabolite of cytarabine-5'-elaidic acid ester and gemcitabine-5'-elaidic acid ester in deficient cancer cells. Once inside the cell the lipid tail of the lipid-conjugated drug such as gemcitabine-5'-elaidic acid ester or cytarabine-5'-elaidic acid ester is cleaved off, and the parent drug is released. With the lack of hENT1 transporter (due to the low expression and/or activity of hENT1 in the identified patient population), the drug is trapped inside the cell, and high concentrations of active metabolites have been measured. (See Adema et al., "Fatty acid derivatives of cytarabine and gemcitabine, CP-4055 and CP-4126, show a prolonged cellular retention compared to the parent drug," Proceedings of the 99th Annual Meeting of the American Association for Cancer Research. Abstract nr 5740 (2008).

These observations indicate that lipid-conjugated gemcitabine derivatives such as gemcitabine-5'-elaidic acid ester and/or lipid-conjugated cytarabine derivatives such as cytarabine-5'-elaidic acid ester are useful in treating tumors that are resistant or otherwise less responsive to cytarabine and gemcitabine due to the lack of hENT1 or low hENT1 expression and/or activity. Thus, the antibodies of the invention are useful in combination therapies with these lipid-conjugated gemcitabine derivatives such as gemcitabine-5'-elaidic acid ester and/or lipid-conjugated cytarabine derivatives such as cytarabine-5'-elaidic acid ester and/or lipid-conjugated as 5-azacytidine-5'-elaidic acid ester. For example, the hENT1 antibodies are useful in detecting patients with low or otherwise reduced hENT1 expression and/or activity. For example, the hENT1 antibodies can be used to screen patients having cancers and other neoplastic disorders such as acute myeloid leukemia (AML) or pancreatic cancer. Thus, the hENT1 antibodies are useful to identify patients for treatment based on the hENT1 expression and/or activity level.

In some embodiments, the patients are currently receiving treatment regimens that include administration of one or more nucleoside analogue drugs and/or drugs derived from nucleoside analogues, such as, pyrimidine derivatives including, for example, cytarabine, gemcitabine, and derivatives thereof, and purine derivatives including, for example, fludarabine, cladribine, clofarabine and derivatives thereof. In some embodiments, the patients are currently receiving treatment regimens that include administration of one or more nucleoside analogue drugs and/or drugs derived from nucleoside analogues, such as pyrimidine derivatives including, for example, cytarabine, gemcitabine, and derivatives thereof d purine derivatives including, for example, fludarabine, cladribine, clofarabine and derivatives thereof, and these patients have stopped responding to treatment or are otherwise less responsive to the nucleoside analogue drug.

In some embodiments, the patients have previously received treatment regimens that included administration of one or more nucleoside analogue drugs and/or drugs derived from nucleoside analogues, such as pyrimidine derivatives including, for example, cytarabine, gemcitabine, and derivatives thereof and purine derivatives including, for example, fludarabine, cladribine, clofarabine and derivatives thereof. In some embodiments, the patients have previously received treatment regimens that included administration of one or more nucleoside analogue drugs and/or drugs derived from nucleoside analogues, such as pyrimidine derivatives including, for example, cytarabine, gemcitabine, and derivatives thereof and purine derivatives including, for example, fludarabine, cladribine, clofarabine and derivatives thereof, and these patients stopped responding to treatment or were otherwise less responsive to the nucleoside analogue drug.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings.

As used herein, the terms "human Equilibrative Nucleoside Transport 1" and "hENT1" are synonymous and may be used interchangeably.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "directed against" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat et al., Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin or fragment thereof, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; e.g., ≤100 nM, preferably ≤10 nM and more preferably ≤1 nM.

As used herein, the terms "specific binding," "immunological binding," and "immunological binding properties" (and all grammatical variations thereof) refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/ antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361: 186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to hENT1, when the equilibrium binding constant ($K_d$) is ≤1 µM, preferably ≤100 nM, more preferably ≤10 nM, and most preferably ≤100 pM to about ≤1 pM, as measured by assays such as radioligand binding assays or similar assays known to those skilled in the art.

The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules presented in SEQ ID NOS: 1, 3, 5, 7, 27, 29, 31, 33, 35 and 37, and nucleic acid molecules encoding the light chain immunoglobulin molecules represented in SEQ ID NOS: 13, 15, 17, 21, 42, 44, 46 and 48.

hENT1 Antibodies

Monoclonal antibodies of the invention bind hENT1. These monoclonal antibodies have the ability to inhibit hENT1 expression and/or activity Inhibition is determined, for example, using any of a variety of standard assays.

Exemplary variable heavy chain sequences for the hENT1 antibodies of the invention include the VH3-12 variable heavy chain, the VH5-9 variable heavy chain, the VH5-12 variable heavy chain, the VH5-13 variable heavy chain, the VH5-3 variable heavy chain, the VH5-11 variable heavy chain, or the consensus variable heavy chain provided herein and referred to as the consensus variable heavy chain region sequence 1 (consensus VH sequence 1). Exemplary variable heavy chain sequences for the hENT1 antibodies of the invention also include the VH1-1 variable heavy chain, the VH1-4 variable heavy chain, the VH1-6 variable heavy chain, the VH4-2 variable heavy chain, the VH4-3 variable heavy chain, the VH4-4 variable heavy chain or the consensus variable heavy chain provided herein and referred to as the consensus variable heavy chain region sequence 2 (consensus VH sequence 2). The variable domain of each heavy chain sequence is shown in bold in the sequences below.

Preferably, the variable heavy chains of the hENT1 antibodies of the invention include a variable heavy chain complementarity determining region 1 (VH CDR1) sequence comprising the amino acid sequence GYTFTDYE (SEQ ID NO: 10), a variable heavy chain complementarity determining region 2 (VH CDR2) sequence comprising the amino acid sequence IDPETGAI (SEQ ID NO: 11) or the amino acid sequence IDPETGKT (SEQ ID NO: 40), and a variable heavy chain complementarity determining region 3 (VH CDR3) sequence comprising the amino acid sequence TREFTY (SEQ ID NO: 12) or the amino acid sequence TRELTY (SEQ ID NO: 41). The CDRs were identified using IMGT algorithms. (Lefranc, et al., Dev. Comp. Immunol., 27, 55-77 (2003); Brochet et al., "IMGT/V-QUEST: the highly customized and integrated system for IG and TR standardized V-J and V-D-J sequence analysis," Nucl. Acids Res., vol. 36: W503-508 (2008)).

The VH3-12 heavy chain variable region (SEQ ID NO: 2) is encoded by the nucleic acid sequence shown in SEQ ID NO: 1. The variable domain is shown in bold in the amino acid sequence shown in SEQ ID NO: 2. The CDR regions are boxed in the amino acid sequence shown in SEQ ID NO: 2.

```
>VH3-12 nucleic acid sequence (SEQ ID NO: 1)

ATGGAATGCACCTGGGTTTTTCTCTTCCTCCTGTCAGTAATTGCAGGTGTCCAATCCCAGGTTC

ATCTGCAGCAGTCTGGGGCTGAGCTGGTGAGGCCTGGGGCTTCAGTGACGCCGCCCTGCAAGGC

TTCGGGCTACACATTTACTGACTATGAAATGCACTGGGTGAAACAGACACCTGTGCATGGCCTG

GAATGGATTGGCGCTATTGATCCTGAAACTGGTGCTATTGTCTACAATCAGAAGTTCAAGGGCA

AGGCCACACTGACTGCAGACAAATCCTCCAACACAGCCCACATGGAGCTCCGCAGCCTGACATC

TGAGGACTCTGCCGTCTATTACTGTACAAGAGAGTTTACTTACTGGGGCCAAGGGACTCTGGTC

ACTGTCTCTGCAGCCAAAACGACACCCCCATCCGTCTTCCCCCTGGCACAAGCCAAATTCTGCA

GATATCCATCACACTGGCGGCCGCTCGAGCATCTATTCTTTGGGAA

>VH3-12 amino acid sequence (SEQ ID NO: 2)

MECTWVFLFLLSVIAGVQSQVHLQQSGAELVRPGASVTPPCKAS|GYTFTDYE|MHWVKQTPVHGL

EWIGA|IDPETGAI|VYNQKFKGKATLTADKSSNTAHMELRSLTSEDSAVYYC|TREFTY|WGQGTLV

TVSAAKTTPPSVFPLAQAKFCRYPSHWRPLEHLFFG
```

The VH5-9 heavy chain variable region (SEQ ID NO:4) is encoded by the nucleic acid sequence shown in SEQ ID NO:3. The variable domain is shown in bold in the amino acid sequence shown in SEQ ID NO: 4. The CDR regions are boxed in the amino acid sequence shown in SEQ ID NO: 4.

```
>VH5-9 nucleic acid sequence (SEQ ID NO: 3)

ATGGAATGCACCTGGGTTATTCTCTTCCTCCTGTCAGTAATTGCAGGTGTCCAATCCCAGGTTC

ATCTGCAGCAGTCTGGGGCTGAGCTGGTGAGGCCTGGGGCTTCAGTGACGCTGCCCTGCAAGGC

TTCGGGCTACACATTTACTGACTATGAAATGCACTGGGTGAAACAGACACCTGTGCATGGCCTG

GAATGGATCGGCGCTATTGATCCTGAAACTGGTGCTATTGTCTACAATCAGAAGCTCAAGGGCA

AGGCCACACTGGCTGCAGACAAATCCTCCAACACAGCCTACATGGAGCTCCGCAGCCTGACATC

TGAGGACTCTGCCGTCTATTACTGTACAAGAGAGTTTACTTACTGGGGCCAAGGGACTCTGGTC

ACTGTCTCTGCAGCCAAAACGACACCCCCACCCGTTTATCCACTGGCCCCCTGGAAGCTTGGG

>VH5-9 amino acid sequence (SEQ ID NO: 4)

MECTWVILFLLSVIAGVQSQVHLQQSGAELVRPGASVTLPCKASGYTFTDYE**MHWVKQTPVHGL

EWIGAIDPETGAIVYNQKLKGKATLAADKSSNTAYMELRSLTSEDSAVYYCREFTY**WGQGTLV

TVSA**AKTTPPPVYPLAPWKLG
```

The VH5-12 heavy chain variable region (SEQ ID NO:6) is encoded by the nucleic acid sequence shown in SEQ ID NO:5. The variable domain is shown in bold in the amino acid sequence shown in SEQ ID NO: 6. The CDR regions are boxed in the amino acid sequence shown in SEQ ID NO: 6.

```
>VH5-12 nucleic acid sequence (SEQ ID NO: 5)
ATGAAATGGACCTGGGTTTTCCTCTTCCTCCTGTCAGTAATTGCAGGTGTCCAATCCCAGGTTC

ATCTGCAGCAGTCTGGGGCTGAGCTGGTGAGGCCTGGGGCTTCAGTGACGCTGCCCTGCAAGGC

TTCGGGCTACACATTTACTGACTATGAAATGCACTGGGTGAAACAGACACCTGTGCATGGCCTG

GAATGGATTGGCGCTATTGATCCTGAAACTGGTGCTATTGTCTACAATCAGAAGTTCAAGGGCA

AGGCCACACTGACTGCAGACAAATCCTCCAACACAGCCTACATGGAGCTCCGCAGCCTGACATC

TGAGGACTCTGCCGTCTATTACTGTACAAGAGAGTTTACTTACTGGGGCCAAGGGACTCTGGTC

ACTGTCTCTGCAGCCAAAACGACACCCCCATCCGTTTATCCACTGGCCCCTGGAAGCTTGGG

>VH5-12 amino acid sequence (SEQ ID NO: 6)

MKWTWVFLFLLSVIAGVQSQVHLQQSGAELVRPGASVTLPCKASGYTFTDYE**MHWVKQTPVHGL

EWIGAIDPETGAIVYNQKFKGKATLTADKSSNTAYMELRSLTSEDSAVYYCREFTY**WGQGTLV

TVSA**AKTTPPSVYPLAPGSL
```

The VH5-13 heavy chain variable region (SEQ ID NO:8) is encoded by the nucleic acid sequence shown in SEQ ID NO:7. The variable domain is shown in bold in the amino acid sequence shown in SEQ ID NO: 8. The CDR regions are boxed in the amino acid sequence shown in SEQ ID NO: 8.

>VH5-13 nucleic acid sequence (SEQ ID NO: 7)

ATGGAATGCAGCAGGGTTATTCTCTTCCTCCTGTCAGTAATTGCAGGTGTCCAATCCCAGGTTC

ATCTGCAGCAGTCTGGGGCTGAGCTGGTGAGGCCTGGGGCTTCAGTGACGCTGCCCTGCAAGGC

TTCGGGCTACACATTTACTGACTATGAAATGCACTGGGTGAAACAGACACCTGTGCATGGCCTG

GAATGGATTGGCGCTATTGATCCTGAAACTGGTGCTATTGTCTACAATCAGAAGTTCAAGGGCA

AGGCCACACTGACTGCAGACAAATCCTCCAACACAGCCTACATGGAGCTCCGCAGCCTGACATC

TGAGGACTCTGCCGTCTATTACTGTACAAGAGAGTTTACTTACTGGGGCCAAGGGACTCTGGTC

ACTGTCTCTGCAGCCAAAACGACACCCCCACCCGTCTATCCCCTGGCCCCTGGAAGCTTGGG

>VH5-13 amino acid sequence (SEQ ID NO: 8)

MECSRVILFLLSVIAGVQSQVHLQQSGAELVRPGASVTLPCKASGYTFTDYE**MHWVKQTPVHGL
EWIGAIDPETGAIVYNQKFKGKATLTADKSSNTAYMELRSLTSEDSAVYYCTREFTYWGQGTLV
TVSA**AKTTPPPVYPLAPGSL

The VH5-3 heavy chain variable region (SEQ ID NO:51) is encoded by the nucleic acid sequence shown in SEQ ID NO:50. The variable domain is shown in bold in the amino acid sequence shown in SEQ ID NO: 51. The CDR regions are boxed in the amino acid sequence shown in SEQ ID NO: 51.

>VH5-3 nucleic acid sequence (SEQ ID NO: 50)

ATGGAATGCACCTGGGTTCTTCTCTTCCTCCTGTCAGTAATTGCAGGTGTCCAATCCCAGGTTC

ATCTGCAGCAGTCTGGGGCTGAGCTGGTGAGGCCTGGGGCTTCAGTGACGCTGCCCTGCAAGGC

TTCGGGCTACACATTTACTGACTATGAAATGCACTGGGTGAAACAGACACCTGTGCATGGCCTG

GAATGGATTGGCGCTATTGATCCTGAAACTGGTGCTATTGTCTACGATCAGAAGTTCAAGGGCA

AGGCCACACTGACTGCAGACAAATCCTCCAACACAGCCTACATGGAGCTCCGCAGCCTGACATC

TGAGGACTCTGCCGTCTATTACTGTACAAGAGAGTTTACTTACTGGGGCCAAGGGACTCTGGTC

ACTGTCTCTGCAGCCAAAACGACACCCCCACCCGTCTATCCCCTGGCCCCTGGAAGCTTGGG

>VH5-3 amino acid sequence (SEQ ID NO: 51)

MECTWVLLFLLSVIAGVQSQVHLQQSGAELVRPGASVTLPCKASGYTFTDYE**MHWVKQTPVHGL
EWIGAIDPETGAIVYDQKFKGKATLTADKSSNTAYMELRSLTSEDSAVYYCTREFTYWGQGTLV
TVSA**AKTTPPPVYPLAPGSL

The VH5-11 heavy chain variable region (SEQ ID NO:53) is encoded by the nucleic acid sequence shown in SEQ ID NO:52. The variable domain is shown in bold in the amino acid sequence shown in SEQ ID NO: 53. The CDR regions are boxed in the amino acid sequence shown in SEQ ID NO: 53.

>VH5-11 nucleic acid sequence (SEQ ID NO: 52)

ATGGGATGGAGCGTGGTTTATCTCTTCCTCCTGTCAGTAATTGCAGGTGTCCAATCCCAGGTTC

ATCTGCAGCAGTCTGGGGCTGAGCTGGTGAGGCCTGGGGCTTCAGTGACGCTGCCCTGCAAGGC

TTCGGGCTACACATTTACTGACTATGAAATGCACTGGGTGAAACAGACACCTGTGCATGGCCTG

GAATGGATTGGCGCTATTGATCCTGAAACTGGTGCTATTGTCTACAATCAGAAGTTCAAGGGCA

```
AGGCCACACTGACTGCAGACAAATCCTCCAACACAGCCTACATGGAGCTCCGCAGCCTGACATC

TGAGGACTCTGCCGTCTATTACTGTACAAGAGAGTTTACTTACTGGGGCCAAGGGACTCTGGTC

ACTGTCTCTGCAGCCAAAACGACACCCCCATCCGTTTATCCCCTGGTCCCTGGAAGCTTGGG

>VH5-11 amino acid sequence(SEQ ID NO: 53)

MGWSVVYLFLLSVIAGVQSQVHLQQSGAELVRPGASVTLPCKASGYTFTDYEMHWVKQTPVHGL

EWIGAIDPETGAIVYNQKFKGKATLTADKSSNTAYMELRSLTSEDSAVYYCTREFTYWGQGTLV

TVSAAKTTPPSVYPLVPGSL
```

The amino acid sequence of the consensus heavy chain variable region sequence 1 is shown in SEQ ID NO: 9. The variable domain is shown in bold in the amino acid sequence shown in SEQ ID NO: 9. The CDR regions are boxed in the amino acid sequence shown in SEQ ID NO: 9.

```
>Consensus VH amino acid sequence 1 (SEQ ID NO: 9)

MECTWVILFLLSVIAGVQSQVHLQQSGAELVRPGASVTLPCKASGYTFTDYEMHWVKQTPVHGL

EWIGAIDPETGAIVYNQKFKGKATLTADKSSNTAYMELRSLTSEDSAVYYCTREFTYWGQGTLV

TVSAAKTTPPSVYPLAPGSL
```

An alignment of these variable heavy chain sequences is shown below:

```
                        1                                                50
VH5-13        (1)  MECSRVILFLLSVIAGVQSQVHLQQSGAELVRPGASVTLPCKASGYTFTD
VH5-9         (1)  MECTWVILFLLSVIAGVQSQVHLQQSGAELVRPGASVTLPCKASGYTFTD
VH5-12        (1)  MKWIWVFLFLLSVIAGVQSQVHLQQSGAELVRPGASVTLPCKASGYTFTD
VH3-12        (1)  MECTWVFLFLLSVIAGVQSQVHLQQSGAELVRPGASVTPPCKASGYTFTD
VH5-3         (1)  MECTWVLLFLLSVIAGVQSQVHLQQSGAELVRPGASVTLPCKASGYTFTD
VH5-11        (1)  MGWSVVYLFLLSVIAGVQSQVHLQQSGAELVRPGASVTLPCKASGYTFTD
                    .****.*..................................*..........
Consensus 1   (1)  MECTWVILFLLSVIAGVQSQVHLQQSGAELVRPGASVTLPCKASGYTFTD 51                                               100
VH5-13       (51)  YEMHWVKQTPVHGLEWIGAIDPETGAIVYNQKFKGKATLTADKSSNTAYM
VH5-9        (51)  YEMHWVKQTPVHGLEWIGAIDPETGAIVYNQKLKGKATLAADKSSNTAYM
VH5-12       (51)  YEMHWVKQTPVHGLEWIGAIDPETGAIVYNQKFKGKATLTADKSSNTAYM
VH3-12       (51)  YEMHWVKQTPVHGLEWIGAIDPETGAIVYNQKFKGKATLTADKSSNTAHM
VH5-3        (51)  YEMHWVKQTPVHGLEWIGAIDPETGAIVYDQKFKGKATLTADKSSNTAYM
VH5-11       (51)  YEMHWVKQTPVHGLEWIGAIDPETGAIVYNQKFKGKATLTADKSSNTAYM
                    ...............................*.......*........*.
Consensus 1  (51)  YEMHWVKQTPVHGLEWIGAIDPETGAIVYNQKFKGKATLTADKSSNTAYM 101                                               150
VH5-13      (101)  ELRSLTSEDSAVYYCTREFTYWGQGTLVTVSAAKTTPPPVYPLAPGSL--
VH5-9       (101)  ELRSLTSEDSAVYYCTREFTYWGQGTLVTVSAAKTTPPPVYPLAPWKLG-
VH5-12      (101)  ELRSLTSEDSAVYYCTREFTYWGQGTLVTVSAAKTTPPSVYPLAPGSL--
VH3-12      (101)  ELRSLTSEDSAVYYCTREFTYWGQGTLVTVSAAKTTPPSVPLAQAKFCR
VH5-3       (101)  ELRSLTSEDSAVYYCTREFTYWGQGTLVTVSAAKTTPPPVYPLAPGSL--
VH5-11      (101)  ELRSLTSEDSAVYYCTREFTYWGQGTLVTVSAAKTTPPSVYPLVPGSL--
                    ......................................*.*...****
Consensus 1 (101)  ELRSLTSEDSAVYYCTREFTYWGQGTLVTVSAAKTTPPSVYPLAPGSL
```

```
              151         164
VH5-13   (149) -------------- (SEQ ID NO: 8)
VH5-9    (150) -------------- (SEQ ID NO: 4)
VH5-12   (149) -------------- (SEQ ID NO: 6)
VH3-12   (151) YPSHWRPLEHLFFG (SEQ ID NO: 2)
VH5-3    (149) -------------- (SEQ ID NO: 51)
VH5-11   (149) -------------- (SEQ ID NO: 53)
Consensus 1 (151) -------------- (SEQ ID NO: 9)
```

The VH1-1 heavy chain variable region (SEQ ID NO: 28) is encoded by the nucleic acid sequence shown in SEQ ID NO: 27. The variable domain is shown in bold in the amino acid sequence shown in SEQ ID NO: 28. The CDR regions are boxed in the amino acid sequence shown in SEQ ID NO: 28.

```
>VH1-1 nucleic acid sequence (SEQ ID NO: 27)

ATGAAATGCAGCTGGGTTTTCCTCTTCCTCCTGTCAGTAATTGCAGGTGTCCAATCCCGGGTTC

AACTGCAGCAGTCTGGGTCTGAGCTGGTGAGGCCTGGGGCTTCAGTGACGCTGTCCTGCAAGGC

TTCGGGCTACACATTTACTGACTATGAAATGCACTGGGTGAAGCAGACACCTGTGCATGGCCTG

GAATGGATTGGAGCGATTGATCCTGAAACTGGTAAAACTGCCTACAATCAGAAGTTCAAGGGCA

AGACCACACTGACTGCAGACAAATCCTCCAGCACAGCCTACATGGAGTTCCGCAGCCTGACATC

TGAGGACTCTGCCGTCCATTACTGTACAAGAGAGTTGACTTACTGGGGCCAAGGGACTCTGGTC

ACTGTCTCTGCAGCCAAAACGACACCCCCATCGGTCTTCCCCCTGGCAC

>VH1-1 amino acid sequence (SEQ ID NO: 28)

MKCSWVFLFLLSVIAGVQSRVQLQQSGSELVRPGASVTLSCKASGYTFTDYE**MHWVKQTPVHGL

EWIGAIDPETGKTAYNQKFKGKTTLTADKSSSTAYMEFRSLTSEDSAVHYCTRELTYWGQGTLV

TVSA**AKTTPPSVFPLA
```

The VH1-4 heavy chain variable region (SEQ ID NO: 30) is encoded by the nucleic acid sequence shown in SEQ ID NO: 29. The variable domain is shown in bold in the amino acid sequence shown in SEQ ID NO: 30. The CDR regions are boxed in the amino acid sequence shown in SEQ ID NO: 30.

```
>VH1-4 nucleic acid sequence (SEQ ID NO: 29)

ATGGAATGCACCTGGGTTTTCCTCTTCCTCCTGTCAGTAATTGCAGGTGTCCAATCCCAGGTTC

AACTGCAGCAGTCTGGGTCTGAGCTGGTGAGGCCTGGGGCTTCAGTGACGCTGTCCTGCAAGGC

TTCGGGCTACACATTTACTGACTATGAAATGCACTGGGTGGAGCAGACACCTGTGCATGGCCTG

GAATGGATTGGAGCGATTGATCCTGAAACTGGTAAAACTGCCTACAATCAGAAGTTCAAGGGCA

AGACCACACTGACTGCAGACAAATCCTCCAGCACAGCCTACATGGAGTTCCGCAGCCTGACATC

TGAGGACTCTGCCGTCCATTACTGTACAAGAGAGTTGACTTACTGGGGCCAAGGGACTCTGGTC

ACTGTCTCTGCAGCCAAAACGACACCCCCATCCGTCTTCCCCCTGGCAC

>VH1-4 amino acid sequence (SEQ ID NO: 30)

MECTWVFLFLLSVIAGVQSQVQLQQSGSELVRPGASVTLSCKASGYTFTDYE**MHWVEQTPVHGL

EWIGAIDPETGKTAYNQKFKGKTTLTADKSSSTAYMEFRSLTSEDSAVHYCTRELTYWGQGTLV

TVSA**AKTTPPSVFPLA
```

The VH1-6 heavy chain variable region (SEQ ID NO: 32) is encoded by the nucleic acid sequence shown in SEQ ID NO: 31. The variable domain is shown in bold in the amino acid sequence shown in SEQ ID NO: 32. The CDR regions are boxed in the amino acid sequence shown in SEQ ID NO: 32.

>VH1-6 nucleic acid sequence (SEQ ID NO: 31)

ATGAAATGCAGCTGGGTTTTCCTCTTCCTCCTGTCAGTAATTGCAGGTGTCCAATCCCAGGTTC

AACTGCAGCAGTCTGGGTCTGAGCTGGTGAGGCCTGGGGCTTCAGTGACGCTGTCCTGCAAGGC

TTCGGGCTACACATTTACTGACTATGAAATGCACTGGGTGAAGCAGACACCTGTGCATGGCCTG

GAATGGATTGGAGCGATTGATCCTGAAACTGGTAAAACTGCCTACAATCAGAAGTTCAAGGGCA

AGACCACACTGACTGCAGACAAATCCCCCAGCACAGCCTACATGGAGTTCCGCAGCCTGACATC

TGAGGACTCTGCCGTCCATTACTGTACAAGAGAGTTGACTTACTGGGGCCAAGGGACTCTGGTC

ACTGTCTCTGCAGCCAAAACGACACCCCCATCGGTCTTCCCCCTGGCAC

>VH1-6 amino acid sequence (SEQ ID NO: 32)

MKCSWVFLFLLSVIAGVQSQVQLQQSGSELVRPGASVTLSCKASGYTFTDYEMHWVKQTPVHGL

EWIGAIDPETGKTAYNQKFKGKTTLTADKSPSTAYMEFRSLTSEDSAVHYCTRELTYWGQGTLV

TVSAAKTTPPSVFPLA

The VH4-2 heavy chain variable region (SEQ ID NO: 34) is encoded by the nucleic acid sequence shown in SEQ ID NO: 33. The variable domain is shown in bold in the amino acid sequence shown in SEQ ID NO: 34. The CDR regions are boxed in the amino acid sequence shown in SEQ ID NO: 34.

>VH4-2 nucleic acid sequence (SEQ ID NO: 33)

ATGAAATGCAGCTGGGTTTTCCTCTTCCTCCTGTCAGTAATTGCAGGTGTCCAATCCCAGGTTC

AACTGCAGCAGTCTGGGTCTGAGCTGGTGAGGCCTGGGGCTTCAGTGACGCTGTCCTGCAAGGC

TTCGGGCTACACATTTACTGACTATGAAATGCACTGGGTGAAGCAGACACCTGTGCATGGCCTG

GAATGGATTGGAGCGATTGATCCTGAAACTGGTAAAACTGCCTACAATCAGAAGTTCAAGGGCA

AGACCACACTGACTGCAGACAAATCCTCCAGCACAGCCTACATGGAGTTCCGCAGCCTGACATC

TGAGGACTCTGCCGTCCATTACTGCACAAGAGAGTTGACTTACTGGGGCCAAGGGACTCTGGTC

ACTGTCTCTGCAGCCAAAACGACACCCCCACCCGTCTATCCATTGGCCCCTGGAAGCTTGGG

>VH4-2 amino acid sequence (SEQ ID NO: 34)

MKCSWVFLFLLSVIAGVQSQVQLQQSGSELVRPGASVTLSCKASGYTFTDYEMHWVKQTPVHGL

EWIGAIDPETGKTAYNQKFKGKTTLTADKSSSTAYMEFRSLTSEDSAVHYCTRELTYWGQGTLV

TVSAAKTTPPPVYPLAPGSL

The VH4-3 heavy chain variable region (SEQ ID NO: 36) is encoded by the nucleic acid sequence shown in SEQ ID NO: 35. The variable domain is shown in bold in the amino acid sequence shown in SEQ ID NO: 36. The CDR regions are boxed in the amino acid sequence shown in SEQ ID NO: 36.

```
>VH4-3 nucleic acid sequence (SEQ ID NO: 35)
```
ATGAAATGGACCTGGGTTTTTCTCTTCCTCCTGTCAGTAATTGCAGGTGTCCAATCCCAGGTTC

AACTGCAGCAGTCTGGGTCTGAGCTGGTGAGGCCTGGGGCTTCAGTGACGCTGTCCTGCAAGGC

TTCGGGCTACACATTTACTGACTATGAAATGCACTGGGTGAAGCAGACACCTGTGCATGGCCTG

GAATGGATTGGAGCGATTGATCCTGAAACTGGTAAAACTGCCTACAATCAGAAGTTCAAGGCA

AGACCACACTGACTGCAGACAAATCCTCCAGCACAGCCTACATGGAGTTCCGCAGCCTGACATC

TGAGGACTCTGCCGTCCATTACTGTACAAGAGAGTTGACTTACTGGGGCCAAGGGACTCTGGTC

ACTGTCTCTGCAGCCAAAACGACACCCCCACCCGTCTATCCCCTGGCCCCTGGAAGCTTGGG

```
>VH4-3 amino acid sequence (SEQ ID NO: 36)
```
MKWTWVFLFLLSVIAGVQSQVQLQQSGSELVRPGASVTLSCKAS|GYTFTDYE|MHWVKQTPVHGL

EWIGA|IDPETGKT|AYNQKFKGKTTLTADKSSSTAYMEFRSLTSEDSAVHYC|TRELTY|WGQGTLV

TVSAAKTTPPPVYPLAPGSL

The VH4-4 heavy chain variable region (SEQ ID NO: 38) is encoded by the nucleic acid sequence shown in SEQ ID NO: 37. The variable domain is shown in bold in the amino acid sequence shown in SEQ ID NO: 38. The CDR regions are boxed in the amino acid sequence shown in SEQ ID NO: 38.

```
>VH4-4 nucleic acid sequence (SEQ ID NO: 37)
```
ATGGAATGGAGCTGGGTTTTCCTCTTCCTCCTGTCAGTAATTGCAGGTGTCCAATCCCAGGTTC

AACTGCAGCAGTCTGGGTCTGAGCTGGTGAGGCCTGGGGCTTCAGTGACGCTGTCCTGCAAGGC

TTCGGGCTACACATTTACTGACTATGAAATGCACTGGGTGAAGCAGACACCTGTGCATGGCCTG

GAATGGATAGGAGCGATTGATCCTGAAACTGGTAAAACTGCCTACAATCAGAAGTTCAAGGCA

AGACCACACTGACTGCAGACAAATCCTCCAGCACAGCCTACATGGAGTTCCGCAGCCTGACATC

TGAGGACTCTGCCGTCCATTACTGTACAAGAGAGTTGACTTACTGGGGCCAAGGGACTCTGGTC

ACTGTCTCTGCAGCCAAAACGACACCCCCACCCGTCTATCCATTGGCCCCCTGGAAGCTTGGG

```
>VH4-4 amino acid sequence (SEQ ID NO: 38)
```
MEWSWVFLFLLSVIAGVQSQVQLQQSGSELVRPGASVTLSCKAS|GYTFTDYE|MHWVKQTPVHGL

EWIGA|IDPETGKT|AYNQKFKGKTTLTADKSSSTAYMEFRSLTSEDSAVHYC|TRELTY|WGQGTLV

TVSAAKTTPPPVYPLAPWKLG

The amino acid sequence of the consensus heavy chain variable region sequence 2 is shown in SEQ ID NO: 39. The variable domain is shown in bold in the amino acid sequence shown in SEQ ID NO: 39. The CDR regions are boxed in the amino acid sequence shown in SEQ ID NO: 39.

```
>Consensus VH amino acid sequence 2 (SEQ ID NO: 39)
```
MKCSWVFLFLLSVIAGVQSQVQLQQSGSELVRPGASVTLSCKAS|GYTFTDYE|MHWVKQTPVHGL

EWIGA|IDPETGKT|AYNQKFKGKTTLTADKSSSTAYMEFRSLTSEDSAVHYC|TRELTY|WGQGTLV

TVSAAKTTPPSVFPLAP

An alignment of these variable heavy chain sequences is shown below:

```
                    1                                                50
VH1-1       (1)   MKCSWVFLFLLSVIAGVQSRVQLQQSGSELVRPGASVTLSCKASGYTFTD
VH1-6       (1)   MKCSWVFLFLLSVIAGVQSQVQLQQSGSELVRPGASVTLSCKASGYTFTD
VH1-6       (1)   MECTWVFLFLLSVIAGVQSQVQLQQSGSELVRPGASVTLSCKASGYTFTD
VH4-2       (1)   MKCSWVFLFLLSVIAGVQSQVQLQQSGSELVRPGASVTLSCKASGYTFTD
VH4-3       (1)   MKWTWVFLFLLSVIAGVQSQVQLQQSGSELVRPGASVTLSCKASGYTFTD
VH4-4       (1)   MEWSWVFLFLLSVIAGVQSQVQLQQSGSELVRPGASVTLSCKASGYTFTD
Consensus 2 (1)   MKCSWVFLFLLSVIAGVQSQVQLQQSGSELVRPGASVTLSCKASGYTFTD 51                                               100
VH1-1       (51)  YEMHWVKQTPVHGLEWIGAIDPETGKTAYNQKFKGKTTLTADKSSSTAYM
VH1-6       (51)  YEMHWVKQTPVHGLEWIGAIDPETGKTAYNQKFKGKTTLTADKSPSTAYM
VH1-4       (51)  YEMHWVEQTPVHGLEWIGAIDPETGKTAYNQKFKGKTTLTADKSSSTAYM
VH4-2       (51)  YEMHWVKQTPVHGLEWIGAIDPETGKTAYNQKFKGKTTLTADKSSSTAYM
VH4-3       (51)  YEMHWVKQTPVHGLEWIGAIDPETGKTAYNQKFKGKTTLTADKSSSTAYM
VH4-4       (51)  YEMHWVKQTPVHGLEWIGAIDPETGKTAYNQKFKGKTTLTADKSSSTAYM
Consensus 2 (51)  YEMHWVKQTPVHGLEWIGAIDPETGKTAYNQKFKGKTTLTADKSSSTAYM 101                              149  (SEQ NO)
VH1-1       (101) EFRSLTSEDSAVHYCTRELTYWGQGTLVTVSAAKTTPPSVFPLA-----  (28)
VH1-6       (101) EFRSLTSEDSAVHYCTRELTYWGQGTLVTVSAAKTTPPSVFPLA-----  (32)
VH1-4       (101) EFRSLTSEDSAVHYCTRELTYWGQGTLVTVSAAKTTPPSVFPLA-----  (30)
VH4-2       (101) EFRSLTSEDSAVHYCTRELTYWGQGTLVTVSAAKTTPPPVYPLAPGSL-  (34)
VH4-3       (101) EFRSLTSEDSAVHYCTRELTYWGQGTLVTVSAAKTTPPPVYPLAPGSL-  (36)
VH4-4       (101) EFRSLTSEDSAVHYCTRELTYWGQGTLVTVSAAKTTPPPVYPLAPWKLG  (38)
Consensus 2 (101) EFRSLTSEDSAVHYCTRELTYWGQGTLVTVSAAKTTPPSVFPLAP   L  (39)
```

Exemplary variable light chain sequences for the hENT1 antibodies of the invention include the VL2 variable light chain, the VL10 variable light chain, the VL11 variable light chain, the VL20 variable light chain, the VL21 light chain, or the consensus variable light chain provided herein and referred to as the consensus variable light chain region sequence 1 (consensus VL sequence 1). Exemplary variable light chain sequences for the hENT1 antibodies of the invention also include the VL2-2 variable light chain, the VL2-3 variable light chain, the VL2-7 variable light chain, the VL2-10 variable light chain, the VL2-12 variable light chain, the VL2-16 variable light chain or the consensus variable light chain provided herein and referred to as the consensus variable light chain region sequence 2 (consensus VL sequence 2).

Preferably, the variable light chains of the hENT1 antibodies of the invention include a variable light chain complementarity determining region 1 (VL CDR1) sequence comprising the amino acid sequence QSLLFSNGKTY (SEQ ID NO: 24), a variable light chain complementarity determining region 2 (VL CDR2) sequence comprising the amino acid sequence LVS (SEQ ID NO: 25), and a variable light chain complementarity determining region 3 (VL CDR3) sequence comprising the amino acid sequence VQGTHFPWT (SEQ ID NO: 26). The CDRs were identified using IMGT algorithms. (Lefranc, et al., Dev. Comp. Immunol., 27, 55-77 (2003); Brochet et al., "IMGT/V-QUEST: the highly customized and integrated system for IG and TR standardized V-J and V-D-J sequence analysis," Nucl. Acids Res., vol. 36: W503-508 (2008)).

The VL2 light chain variable region (SEQ ID NO: 14) is encoded by the nucleic acid sequence shown in SEQ ID NO: 13. The variable domain is shown in bold in the amino acid sequence shown in SEQ ID NO: 14. The CDR regions are boxed in the amino acid sequence shown in SEQ ID NO: 14.

```
>VL2 nucleic acid sequence (SEQ ID NO: 13)

TCTCCTTTCAACAAAGCACATTTCGATTTCCAGCTTGGTGCCTCCACCGAACGTCCACGGAAAA

TGTGTACCTTGCACGCAGTAATAAACTCCCAAATCCTCAGCCTCCACTCTGCTGATTTTCAGTG

AAAAATCTGTTCCTGAACCAGTGCCAGTGAACCTGTCAGGGACTCCAGAGTTCAGTTTAGACAC

CAGATAGATTAGGCGCTTTGGAGACTGGCCTGGCCTCTGAAATAACCAATTCAAGTAGGTTTTT

CCATTACTAAATAAGAGGCTCTGACTTGACCTGCAAGAGACAGAGGCTGGTTGTCCAATGGTAA

CCGACAAAGTGAGTGGAGTTTGGGTCATCAAAACATC

>VL2 amino acid sequence (SEQ ID NO: 14)

DVLMTQTPLTLSVTIGQPASVSCRSSQSLLFSNGKTYLNWLFQRPGQSPKRLIYLVSKLNSGVP

DRFTGTGSGTDFSLKISRVEAEDLGVYYCVQGTHFPWTFGGGTKLEIEMCFVERR
```

The VL10 light chain variable region (SEQ ID NO: 16) is encoded by the nucleic acid sequence shown in SEQ ID NO: 15. The CDR regions are boxed in the amino acid sequence shown in SEQ ID NO: 16.

```
>VL10 nucleic acid sequence (SEQ ID NO: 15)
ATTGGATATCCTCGCAGCATCTCGGCTTGATGTTTTGATGACCCAAACTCCACTCACTTTGTCG
GTTACCATTGGACAACCAGCCTCTGTCTCTTGCAGGTCAAGTCAGAGCCTCTTATTTAGTAATG
GAAAAACCTATTTGAATTGGTTATTTCAGAGGCCAGGCCAGTCTCCAAAGCGCCTAATCTATCT
GGTGTCTAAACTGAACTCTGGAGTCCCTGACAGGTTCACTGGCACTGGTTCAGGAACAGATTTT
TCACTGAAAATCAGCAGAGTGGAGGCTGAGGATTTGGGAGTTTATTACTGCGTGCAAGGTACAC
ATTTTCCGTGGACGTTCGGTGGAGGCACCAAGCTGGAAATCAAACGG >VL10 amino acid sequence (SEQ ID NO: 16)
LDILAASRLDVLMTQTPLTLSVTIGQPASVSCRSS QSLLFSNGKTY LNWLFQRPGQSPKRLIY L
VS KLNSGVPDRFTGTGSGTDFSLKISRVEAEDLGVYYC VQGTHFPWT FGGGTKLEIKR
```

The VL11 light chain variable region (SEQ ID NO: 18) is encoded by the nucleic acid sequence shown in SEQ ID NO: 17. The CDR regions are boxed in the amino acid sequence shown in SEQ ID NO: 18.

```
>VL11 nucleic acid sequence (SEQ ID NO: 17)
CTTTCGCGATGATCCTTGCACGCATTTCAGGCTTGGATGTTTTGATGACCCAAACTCCACTCAC
TTTGTCGGTTACCATTGGACAACCAGCCTCTGTCTCTTGCAGGTCAAGTCAGAGCCTCTTATTT
AGTAATGGAAAAACCTATTTGAATTGGTTATTTCAGAGGCCAGGCCAGTCTCCAAAGCGCCTAA
TCTGTCTGGTGTCTAAACTGAACTCTGGAGTCCCTGACAGGTTCACTGGCACTGGTTCAGGAAC
AGATTTTTCACTGAAAATCAGCAGAGTGGAGGCTGAGGATTTGGGATTTTATTACTGCGTGCAA
GGTACACATTTTCCGTGGACGTTCGGTGGAGGCACCAAGCTGGAAATCAAACGG >VL11 amino acid sequence (SEQ ID NO: 18)
FAMILARISGLDVLMTQTPLTLSVTIGQPASVSCRSS QSLLFSNGKTY LNWLFQRPGQSPKRLI
C LVS KLNSGVPDRFTGTGSGTKFSLKISRVEAEDLGFYYC VQGTHFPWT FGGGTKLEIKR
```

The VL20 light chain variable region (SEQ ID NO: 20) is encoded by the nucleic acid sequence shown in SEQ ID NO: 19. The variable domain is shown in bold in the amino acid sequence shown in SEQ ID NO: 20. The CDR regions are boxed in the amino acid sequence shown in SEQ ID NO: 20.

```
>VL20 nucleic acid sequence (SEQ ID NO: 19)
GATGTTTTGATGACCCAAACTCCACTCACTTTGTCGGTTACCATTGGACAACCAGCCTCTGTCT
CTTGCAGGTCAAGTCAGAGCCTCTTATTTAGTAATGGAAAAACCTATTTGAATTGGTTATTTCA
GAGGCCAGGCCAGTCTCCAAAGCGCCTAATCTATCTGGTGTCTAAACTGAACTCTGGAGTCTCT
GACAGGTTCACTGGCACTGGTTCAGAAACAGATTTTTCACTGAAAATCAGCAGAGTGGAGGCTG
AGGATTTGGGAGTTTATTACTGCGTGCAAGGTACATATTTTCCGTGGACGTTCGGTGGAGGCAC
```

```
CAAGCTGGAAATCAAACGGCCCTTTTTAATTCTGCAGATATCCTATCACAACGTTGCTGGCCGC

GGCCGCT

>VL20 amino acid sequence (SEQ ID NO: 20)

DVLMTQTPLTLSVTIGQPASVSCRSSQSLLFSNGKTYLNWLFQRPGQSPKRLIYLVSKLNSGVS

DRFTGTGSETDFSLKISRVEAEDLGVYYCVQGTYFPWTFGGGTKLEIKRPFLILQISYHNVAGR

GR
```

The VL21 light chain variable region (SEQ ID NO: 22) is encoded by the nucleic acid sequence shown in SEQ ID NO: 21. The variable domain is shown in bold in the amino acid sequence shown in SEQ ID NO: 22. The CDR regions are boxed in the amino acid sequence shown in SEQ ID NO: 21.

```
>VL21 nucleic acid sequence (SEQ ID NO: 21)

GATGTTTTGATGACCCAAACTCCACTCACTTTGTCGGTTACCATTGGACAACCAGCCTCTGTCT

CTTGCAGGTCAAGTCAGAGCCTCTTATTTAGTAATGGAAAAACCTATTTGAATTGGTTATTTCA

GAGGCCAGGCCAGTCTCCAAAGCGCCTAATCTATCTGGTGTCTAAACTGAACTCTGGAGTCCCT

GACAGGTTCACCGGCACTGGTTCAGGAACAGATTTTCCACTGAAAATCAGCAGAGTGGAGGCTG

AGGATTTGGGAGTTTATTACTGCGTGCAAGGTACACATTTTCCGTGGACGTTCGGTGCCCTTTT

TAAAGGAGGCCGTGATAAAAAAT

>VL21 amino acid sequence (SEQ ID NO: 22)

DVLMTQTPLTLSVTIGQPASVSCRSSQSLLFSNGKTYLNWLFQRPGQSPKRLIYLVSKLNSGVP

DRFTGTGSGTDFPLKISRVEAEDLGVYYCVQGTHFPWTFGALFKGGRDKK
```

The consensus light chain variable region sequence 1 is encoded by the nucleic acid sequence shown in SEQ ID NO: 23. The CDR regions are boxed in the amino acid sequence shown in SEQ ID NO: 23.

```
>Consensus VL amino acid sequence 1 (SEQ ID NO: 23)

DVLMTQTPLTLSVTIGQPASVSCRSSQSLLFSNGKTYLNWLFQRPGQSPKRLIYLVSKLNSGVP

DRFTGTGSGTDFSLKISRVEAEDLGVYYCVQGTHFPWTFGGGTKLEIKR
```

An alignment of these variable light chain sequences is shown below:

```
                      12                                                        61
      VL21       (1)  DVLMTQTPLTLSVTIGQPASVSCRSSQSLLFSNGKTYLNWLFQRPGQSPK
      VL10      (10)  DVLMTQTPLTLSVTIGQPASVSCRSSQSLLFSNGKTYLNWLFQRPGQSPK
       VL2       (1)  DVLMTQTPLTLSVTIGQPASVSCRSSQSLLFSNGKTYLNWLFQRPGQSPK
      VL20       (1)  DVLMTQTPLTLSVTIGQPASVSCRSSQSLLFSNGKTYLNWLFQRPGQSPK
      VL11      (12)  DVLMTQTPLTLSVTIGQPASVSCRSSQSLLFSNGKTYLNWLFQRPGQSPK
 Consensus 1    (12)  DVLMTQTPLTLSVTIGQPASVSCRSSQSLLFSNGKTYLNWLFQRPGQSPK
```

```
                 62                                                    111
    VL21   (51)  RLIYLVSKLNSGVPDRFTGTGSGTDFPLKISRVEAEDLGVYYCVQGTHFP
    VL10   (60)  RLIYLVSKLNSGVPDRFTGTGSGTDFSLKISRVEAEDLGVYYCVQGTHFP
     VL2   (51)  RLIYLVSKLNSGVPDRFTGTGSGTDFSLKISRVEAEDLGVYYCVQGTHFP
    VL20   (51)  RLIYLVSKLNSGVSDRFTGTGSETDFSLKISRVEAEDLGVYYCVQGTYFP
    VL11   (62)  RLICLVSKLNSGVPDRFTGTGSGTDFSLKISRVEAEDLGFYYCVQGTHFP
Consensus 1 (62) RLIYLVSKLNSGVPDRFTGTGSGTDFSLKISRVEAEDLGVYYCVQGTHFP 112        124
    VL21   (101) WTFGALFKGGRDK    (SEQ ID NO: 22)
    VL10   (110) WTFGGGTKLEIKR    (SEQ ID NO: 16)
     VL2   (101) WTFGGGTKLEIEM    (SEQ ID NO: 14)
    VL20   (101) WTFGGGTKLEIKR    (SEQ ID NO: 20)
    VL11   (112) WTFGGGTKLEIKR    (SEQ ID NO: 18)
Consensus 1 (112) WTFGGGTKLEIKR   (SEQ ID NO: 23)
```

The VL2-2 light chain variable region (SEQ ID NO: 43) is encoded by the nucleic acid sequence shown in SEQ ID NO: 42. The variable domain is shown in bold in the amino acid sequence shown in SEQ ID NO: 43. The CDR regions are boxed in the amino acid sequence shown in SEQ ID NO: 43.

```
>VL2-2 nucleic acid sequence (SEQ ID NO: 42)

ATGAAGTTGCCTGTTAGGCTGTTGGTGCTGATGTTCTGGATTCCCGCCTCCTCCTCCGACGTGC

TGATGACCCAGACCCCCCTGACCCTGTCCGTGACCATCGGCCAGCCTGCCTCCGTGTCCTGCCG

GTCCTCCCAGTCCCTGCTGTTCTCCAACGGCAAGACCTACCTGAACTGGCTGTTCCAGCGGCCT

GGCCAGTCCCCCAAGCGGCTGATCTACCTGGTGTCCAAGCTGAACTCCGGCGTGCCCGACCGGT

TTACAGGCACCGGCTCTGGCACCGACTTCAGCCTGAAGATCAGCCGGGTGGAAGCCGAGGACCT

GGGCGTGTACTACTGCGTGCAGGGCACCCACTTCCCTTGGACCTTCGGCGGAGGCACCAAGCTG

GAAATCAAGCGGGCCGATGCCGCCCCTACCGTGTCCATCTTCCCACCCTCCAGCGAGCAGCTGA

CCTCTGGCGGCGCTTCCGTCGTGTGCTTCCTGAACAACTTCTACCCCAAAG

>VL2-2 amino acid sequence (SEQ ID NO: 43)

MKLPVRLLVLMFWIPASSSDVLMTQTPLTLSVTIGQPASVSCRSSQSLLFSNGKTY**LNWLFQRP

GQSPKRLIYLVSKLNSGVPDRFTGTGSGTDFSLKISRVEAEDLGVYYCVQGTHFPWTFGGGTKL

EIKR**ADAAPTVSIFPPSSEQLTSGGASVVCFLNNFYPK
```

The VL2-3 light chain variable region (SEQ ID NO: 45) is encoded by the nucleic acid sequence shown in SEQ ID NO: 44. The variable domain is shown in bold in the amino acid sequence shown in SEQ ID NO: 45. The CDR regions are boxed in the amino acid sequence shown in SEQ ID NO: 45.

```
>VL2-3 nucleic acid sequence (SEQ ID NO: 44)

ATGAAGTTGCCTGTTAGGCTGTTGGTGCTGATGTTCTGGATTCCCGCCTCCTCCTCCGACGTGC

TGATGACCCAGACCCCCCTGACCCTGTCCGTGACCATCGGCCAGCCTGCCTCTGTGTCCTGCCG

GTCCTCCCAGTCCCTGCTGTTCTCCAACGGCAAGACCTACCTGAACTGGCTGTTCCAGCGGCCT

GGCCAGTCCCCCAAGCGGCTGATCTACCTGGTGTCCAAGCTGAACTCCGGCGTGCCCGACCGGT

TTACAGGCACCGGCTCTGGCACCGACTTCAGCCTGAAGATCAGCCGGGTGGAAGCCGAGGACCT

GGGCGTGTACTACTGCGTGCAGGGCACCCACTTCCCTTGGACCTTCGGCGGAGGCACCAAGCTG

GAAATCAAGCGGGCCGATGCCGCCCCTACCGTGTCCATCTTCCCACCCTCCAGCGAGCAGCTGA

CCTCTGGCGGCGCTTCCGTCGTGTGCTTCCTGAACAACTTCTACCCCAGAGA
```

-continued

>VL2-3 amino acid sequence (SEQ ID NO: 45)

MKLPVRLLVLMFWIPASSSDVLMTQTPLTLSVTIGQPASVSCRSS[QSLLFSNGKTY]**LNWLFQRP
GQSPKRLIY[LVS]KLNSGVPDRFTGTGSGTDFSLKISRVEAEDLGVYYC[VQGTHFPWTF]GGGTKL
EIKR**ADAAPTVSIFPPSSEQLTSGGASVVCFLNNFYPR

The VL2-7 light chain variable region (SEQ ID NO: 45) is encoded by the nucleic acid sequence shown in SEQ ID NO: 44. The variable domain is shown in bold in the amino acid sequence shown in SEQ ID NO: 45. The CDR regions are boxed in the amino acid sequence shown in SEQ ID NO: 45.

>VL2-7 nucleic acid sequence (SEQ ID NO: 44)

ATGAAGTTGCCTGTTAGGCTGTTGGTGCTGATGTTCTGGATTCCCGCCTCCTCCTCCGACGTGC
TGATGACCCAGACCCCCCTGACCCTGTCCGTGACCATCGGCCAGCCTGCCTCTGTGTCCTGCCG
GTCCTCCCAGTCCCTGCTGTTCTCCAACGGCAAGACCTACCTGAACTGGCTGTTCCAGCGGCCT
GGCCAGTCCCCCAAGCGGCTGATCTACCTGGTGTCCAAGCTGAACTCCGGCGTGCCCGACCGGT
TTACAGGCACCGGCTCTGGCACCGACTTCAGCCTGAAGATCAGCCGGGTGGAAGCCGAGGACCT
GGGCGTGTACTACTGCGTGCAGGGCACCCACTTCCCTTGGACCTTCGGCGGAGGCACCAAGCTG
GAAATCAAGCGGGCCGATGCCGCCCCTACCGTGTCCATCTTCCCACCCTCCAGCGAGCAGCTGA
CCTCTGGCGGCGCTTCCGTCGTGTGCTTCCTGAACAACTTCTACCCCAGAGA

>VL2-7 amino acid sequence (SEQ ID NO: 45)

MKLPVRLLVLMFWIPASSSDVLMTQTPLTLSVTIGQPASVSCRSS[QSLLFSNGKTY]**LNWLFQRP
GQSPKRLIY[LVS]KLNSGVPDRFTGTGSGTDFSLKISRVEAEDLGVYYC[VQGTHFPWTF]GGGTKL
EIKR**ADAAPTVSIFPPSSEQLTSGGASVVCFLNNFYPR

The VL2-10 light chain variable region (SEQ ID NO: 47) is encoded by the nucleic acid sequence shown in SEQ ID NO: 46. The variable domain is shown in bold in the amino acid sequence shown in SEQ ID NO: 47. The CDR regions are boxed in the amino acid sequence shown in SEQ ID NO: 47.

>VL2-10 nucleic acid sequence (SEQ ID NO: 46)

ATGAAGTTGCCTGTAGGCTGTTGGTGCTGATGTTCTGGATTCCCGCCTCCTCCTCCGACGTGCA
GATGACCCAGACCCCCCTGACCCTGTCCGTGACCATCGGCCAGCCTGCCTCTGTGTCCTGCCGG
TCCTCCCAGTCCCTGCTGTTCTCCAACGGCAAGACCTACCTGAACTGGCTGTTCCAGCGGCCTG
GCCAGTCCCCCAAGCGGCTGATCTACCTGGTGTCCAAGCTGAACTCCGGCGTGCCCGACCGGTT
TACAGGCACCGGCTCTGGCACCGACTTCAGCCTGAAGATCAGCCGGGTGGAAGCCGAGGACCTG
GGCGTGTACTACTGCGTGCAGGGCACCCACTTCCCTTGGACCTTCGGCGGAGGCACCAAGCTGG
AAATCAAGCGGGCCGATGCCGCCCCTACCGTGTCCATCTTCCCACCCTCCAGCGAGCAGCTGAC
CTCTGGCGGCGCTTCCGTCGTGTGCTTCCTGAACAACTTCTACCCCAGAGA

>VL2-10 amino acid sequence (SEQ ID NO: 47)

EVACRLLVLMFWIPASSSDVQMTQTPLTLSVTIGQPASVSCRSS[QSLLFSNGKTY]**LNWLFQRPG
QSPKRLIY[LVS]KLNSGVPDRFTGTGSGTDFSLKISRVEAEDLGVYYC[VQGTHFPWTF]GGGTKLE
IKR**ADAAPTVSIFPPSSEQLTSGGASVVCFLNNFYPR

The VL2-12 light chain variable region (SEQ ID NO: 43) is encoded by the nucleic acid sequence shown in SEQ ID NO: 48. The variable domain is shown in bold in the amino acid sequence shown in SEQ ID NO: 43. The CDR regions are boxed in the amino acid sequence shown in SEQ ID NO: 43.

```
>VL2-12 nucleic acid sequence (SEQ ID NO: 48)
ATGAAGTTGCCTGTTAGGCTGTTGGTGCTGATGTTCTGGATTCCCGCCTCCTCCTCCGACGTGC
TGATGACCCAGACCCCCCTGACCCTGTCCGTGACCATCGGCCAGCCTGCCTCTGTGTCCTGCCG
GTCCTCCCAGTCCCTGCTGTTCTCCAACGGCAAGACCTACCTGAACTGGCTGTTCCAGCGGCCT
GGCCAGTCCCCCAAGCGGCTGATCTACCTGGTGTCCAAGCTGAACTCCGGCGTGCCCGACCGGT
TTACAGGCACCGGCTCTGGCACCGACTTCAGCCTGAAGATCAGCCGGGTGGAAGCCGAGGACCT
GGGCGTGTACTACTGCGTGCAGGGCACCCACTTCCCTTGGACCTTCGGCGGAGGCACCAAGCTG
GAAATCAAGCGGGCCGATGCCGCCCCTACCGTGTCCATCTTCCCACCCTCCAGCGAGCAGCTGA
CCTCTGGCGGCGCTTCCGTCGTGTGCTTCCTGAACTTCTACCCCAAAGA
>VL2-12 amino acid sequence (SEQ ID NO: 43)
MKLPVRLLVLMFWIPASSSDVLMTQTPLTLSVTIGQPASVSCRSS[QSLLFSNGKTY]**LNWLFQRP
GQSPKRLIY[LVS]KLNSGVPDRFTGTGSGTDFSLKISRVEAEDLGVYYC[VQGTHFPWT]FGGGTKL
EIKR**ADAAPTVSIFPPSSEQLTSGGASVVCFLNNFYPK
```

The VL2-16 light chain variable region (SEQ ID NO: 45) is encoded by the nucleic acid sequence shown in SEQ ID NO: 44. The variable domain is shown in bold in the amino acid sequence shown in SEQ ID NO: 45. The CDR regions are boxed in the amino acid sequence shown in SEQ ID NO: 45.

```
>VL2-16 nucleic acid sequence (SEQ ID NO: 44)
ATGAAGTTGCCTGTTAGGCTGTTGGTGCTGATGTTCTGGATTCCCGCCTCCTCCTCCGACGTGC
TGATGACCCAGACCCCCCTGACCCTGTCCGTGACCATCGGCCAGCCTGCCTCTGTGTCCTGCCG
GTCCTCCCAGTCCCTGCTGTTCTCCAACGGCAAGACCTACCTGAACTGGCTGTTCCAGCGGCCT
GGCCAGTCCCCCAAGCGGCTGATCTACCTGGTGTCCAAGCTGAACTCCGGCGTGCCCGACCGGT
TTACAGGCACCGGCTCTGGCACCGACTTCAGCCTGAAGATCAGCCGGGTGGAAGCCGAGGACCT
GGGCGTGTACTACTGCGTGCAGGGCACCCACTTCCCTTGGACCTTCGGCGGAGGCACCAAGCTG
GAAATCAAGCGGGCCGATGCCGCCCCTACCGTGTCCATCTTCCCACCCTCCAGCGAGCAGCTGA
CCTCTGGCGGCGCTTCCGTCGTGTGCTTCCTGAACAACTTCTACCCCAGAGA
>VL2-16 amino acid sequence (SEQ ID NO: 45)
MKLPVRLLVLMFWIPASSSDVLMTQTPLTLSVTIGQPASVSCRSS[QSLLFSNGKTY]**LNWLFQRP
GQSPKRLIY[LVS]KLNSGVPDRFTGTGSGTDFSLKISRVEAEDLGVYYC[VQGTHFPWT]FGGGTKL
EIKR**ADAAPTVSIFPPSSEQLTSGGASVVCFLNNFYPR
```

The consensus light chain variable region sequence 2 is encoded by the nucleic acid sequence shown in SEQ ID NO: 49. The variable domain is shown in bold in the amino acid sequence shown in SEQ ID NO: 49. The CDR regions are boxed in the amino acid sequence shown in SEQ ID NO: 49.

>Consensus VL amino acid sequence 2 (SEQ ID NO: 49)

MKLPVRLLVLMFWIPASSSDVLMTQTPLTLSVTIGQPASVSCRSSQSLLFSNGKTYLNWLFQRP

GQSPKRLIYLVSKLNSGVPDRFTGTGSGTDFSLKISRVEAEDLGVYYCVQGTHFPWTFGGGTKL

EIKRADAAPTVSIFPPSSEQLTSGGASVVCFLNNFYPR

An alignment of these variable light chain sequences is shown below:

```
                        1                                                50
     VL2-16   (1)   MKLPVRLLVLMFWIPASSSDVLMTQTPLTLSVTIGQPASVSCRSSQSLLF
     VL2-12   (1)   MKLPVRLLVLMFWIPASSSDVLMTQTPLTLSVTIGQPASVSCRSSQSLLF
      VL2-2   (1)   MKLPVRLLVLMFWIPASSSDVLMTQTPLTLSVTIGQPASVSCRSSQSLLF
      VL2-7   (1)   MKLPVRLLVLMFWIPASSSDVLMTQTPLTLSVTIGQPASVSCRSSQSLLF
     VL2-10   (1)   -EVACRLLVLMFWIPASSSDVQMTQTPLTLSVTIGQPASVSCRSSQSLLF
      VL2-3   (1)   MKLPVRLLVLMFWIPASSSDVLMTQTPLTLSVTIGQPASVSCRSSQSLLF
  Consensus   (1)   MKLPVRLLVLMFWIPASSSDVLMTQTPLTLSVTIGQPASVSCRSSQSLLF 51                                               100
     VL2-16  (51)   SNGKTYLNWLFQRPGQSPKRLIYLVSKLNSGVPDRFTGTGSGTDFSLKIS
     VL2-12  (51)   SNGKTYLNWLFQRPGQSPKRLIYLVSKLNSGVPDRFTGTGSGTDFSLKIS
      VL2-2  (51)   SNGKTYLNWLFQRPGQSPKRLIYLVSKLNSGVPDRFTGTGSGTDFSLKIS
      VL2-7  (51)   SNGKTYLNWLFQRPGQSPKRLIYLVSKLNSGVPDRFTGTGSGTDFSLKIS
     VL2-10  (51)   SNGKTYLNWLFQRPGQSPKRLIYLVSKLNSGVPDRFTGTGSGTDFSLKIS
      VL2-3  (51)   SNGKTYLNWLFQRPGQSPKRLIYLVSKLNSGVPDRFTGTGSGTDFSLKIS
  Consensus  (51)   SNGKTYLNWLFQRPGQSPKRLIYLVSKLNSGVPDRFTGTGSGTDFSLKIS 101                                               150
     VL2-16 (101)   RVEAEDLGVYYCVQGTHFPWTFGGGTKLEIKRADAAPTVSIFPPSSEQLT
     VL2-12 (101)   RVEAEDLGVYYCVQGTHFPWTFGGGTKLEIKRADAAPTVSIFPPSSEQLT
      VL2-2 (101)   RVEAEDLGVYYCVQGTHFPWTFGGGTKLEIKRADAAPTVSIFPPSSEQLT
      VL2-7 (101)   RVEAEDLGVYYCVQGTHFPWTFGGGTKLEIDRADAAPTVSIFPPSSEQLT
     VL2-10 (100)   RVEAEDLGVYYCVQGTHFPWTFGGGTKLEIKRADAAPTVSIFPPSSEQLT
      VL2-3 (101)   RVEAEDLGVYYCVQGTHFPWTFGGGTKLEIKRADAAPTVSIFPPSSEQLT
  Consensus (101)   RVEAEDLGVYYCVQGTHFPWTFGGGTKLEIKRADAAPTVSIFPPSSEQLT 151         166
     VL2-16 (151)   SGGASVVCFLNNFYPR    (SEQ ID NO: 45)
     VL2-12 (151)   SGGASVVCFLNNFYPK    (SEQ ID NO: 43)
      VL2-2 (151)   SGGASVVCFLNNFYPK    (SEQ ID NO: 43)
      VL2-7 (151)   SGGASVVCFLNNFYPK    (SEQ ID NO: 45)
     VL2-10 (150)   SGGASVVCFLNNFYPR    (SEQ ID NO: 47)
      VL2-3 (151)   SGGASVVCFLNNFYPR    (SEQ ID NO: 45)
  Consensus (151)   SGGASVVCFLNNFYPR    (SEQ ID NO: 49)
```

Also included in the invention are antibodies that bind to the same epitope as the antibodies described herein. For example, antibodies of the invention specifically bind to hENT1, wherein the antibody binds to an epitope that includes one or more amino acid residues on human hENT1 (see e.g., Accession Nos. AAC51103.1; NP_001071645.1; NP_001071644.1; NP_0010171643.1; NP_001071642.1; NP_004946.1; NP_001523.2; AAM11785.1; AAF02777.1).

Those skilled in the art will recognize that it is possible to determine, without undue experimentation, if a monoclonal antibody has the same specificity as a monoclonal antibody of the invention by ascertaining whether the former prevents the latter from binding to hENT1. If the monoclonal antibody being tested competes with the monoclonal antibody of the invention, as shown by a decrease in binding by the monoclonal antibody of the invention, then the two monoclonal antibodies bind to the same, or a closely related, epitope.

An alternative method for determining whether a monoclonal antibody has the specificity of monoclonal antibody of the invention is to pre-incubate the monoclonal antibody of the invention with soluble hENT1 protein and then add the monoclonal antibody being tested to determine if the monoclonal antibody being tested is inhibited in its ability to bind hENT1. If the monoclonal antibody being tested is inhibited then, in all likelihood, it has the same, or functionally equivalent, epitopic specificity as the monoclonal antibody of the invention. Screening of monoclonal antibodies of the invention, can be also carried out, e.g., by measuring and determining whether the test monoclonal antibody is able to modulate, block, inhibit, reduce, antagonize, neutralize or otherwise interfere with hENT1 expression and/or activity.

Various procedures known within the art may be used for the production of monoclonal antibodies directed against hENT1, or against derivatives, fragments, analogs homologs or orthologs thereof (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies," or "fully human antibodies" herein. Human monoclonal antibodies are prepared, for example, by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96). Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The antibodies of the invention are monoclonal antibodies. Monoclonal antibodies that modulate, block, inhibit, reduce, antagonize, neutralize or otherwise interfere with hENT1 expression and/or activity are generated, e.g., by immunizing an animal with hENT1 such as, for example, murine, rat or human hENT1 or an immunogenic fragment, derivative or variant thereof. Alternatively, the animal is immunized with cells transfected with a vector containing a nucleic acid molecule encoding hENT1, such that hENT1 is expressed and associated with the surface of the transfected cells. Alternatively, the antibodies are obtained by screening a library that contains antibody or antigen binding domain sequences for binding to hENT1. This library is prepared, e.g., in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to hENT1.

Monoclonal antibodies of the invention include fully human antibodies or humanized antibodies. These antibodies are suitable for administration to humans without engendering an immune response by the human against the administered immunoglobulin.

In some methods, a hENT1 antibody is developed, for example, using phage-display methods using antibodies containing only human sequences. Such approaches are well-known in the art, e.g., in WO92/01047 and U.S. Pat. No. 6,521,404, which are hereby incorporated by reference. (See also Wright et al. Crit, Reviews in Immunol. 12125-168 (1992), Hanes and Pliickthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743).

Human anti-mouse antibody (HAMA) responses have led the industry to prepare chimeric or otherwise humanized antibodies. While chimeric antibodies have a human constant region and an immune variable region, it is expected that certain human anti-chimeric antibody (HACA) responses will be observed, particularly in chronic or multi-dose utilizations of the antibody. Thus, it would be desirable to provide fully human antibodies against hENT1 in order to vitiate or otherwise mitigate concerns and/or effects of HAMA or HACA response.

The production of antibodies with reduced immunogenicity is also accomplished via humanization, chimerization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92/102190 and U.S. Pat. Nos. 5,530,101, 5,585,089, 5,693, 761, 5,693,792, 5,714,350, and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

The invention also includes $F_v$, $F_{ab}$, $F_{ab'}$ and $F_{(ab')2}$ anti-hENT1 fragments, single chain anti-hENT1 antibodies, bispecific anti-hENT1 antibodies, and heteroconjugate anti-hENT1 antibodies.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

It can be desirable to modify the antibody of the invention with respect to effector function, so as to enhance, e.g., the effectiveness of the antibody in treating diseases and disorders associated with aberrant hENT1 expression and/or activity. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Those of ordinary skill in the art will recognize that a large variety of possible moieties can be coupled to the resultant antibodies of the invention. (See, for example, "Conjugate Vaccines," Contributions to Microbiology and Immunology, J. M. Cruse and R. E. Lewis, Jr (eds), Carger Press, New York, (1989), the entire contents of which are incorporated herein by reference). Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding.

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Use of Antibodies Against hENT1

It will be appreciated that administration of therapeutic entities in accordance with the invention will be administered with suitable pharmaceutically acceptable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers or diluents include, but are not limited to, water, saline, ringer's solutions, dextrose solution, and 5% human serum albumin. Liposomes and non-aqueous vehicles such as fixed oils may also be used.

Any of the foregoing mixtures may be appropriate in treatments and therapies in accordance with the present invention, provided that the active ingredient in the formulation is not inactivated by the formulation and the formulation is physiologically compatible and tolerable with the route of administration. A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. The pharmaceutical compositions can be included in a container, pack, or dispenser together with instructions for administration.

A therapeutically effective amount of an antibody of the invention relates generally to the amount needed to achieve a therapeutic objective. The amount required to be administered will depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Efficaciousness of treatment is determined in association with any known method for diagnosing or treating the particular cancer or neoplastic disorder. Alleviation of one or more symptoms of the cancer or neoplastic disorder indicates that the antibody confers a clinical benefit.

In another embodiment, antibodies directed against hENT1 may be used in methods known within the art relating to the localization and/or quantitation of hENT1 (e.g., for use in measuring levels of the hENT1 within appropriate physiological samples, for use in diagnostic methods, for use in imaging the protein, and the like). In yet another embodiment, an antibody according to the invention can be used as an agent for detecting the presence of hENT1 (or a protein fragment thereof) in a sample. In another embodiment, an antibody specific for hENT1 can be used to isolate a hENT1 polypeptide by standard techniques, such as immunoaffinity, chromatography or immunoprecipitation. Detection can be facilitated by coupling (i.e., physically linking) the antibody to a detectable substance. Examples of detectable substances include various enzymes (e.g., horseradish peroxidase, alkaline phosphatase, β-galactosidase, or acetylcholinesterase), prosthetic groups (e.g., streptavidin/biotin and avidin/biotin), fluorescent materials (e.g., umbelliferone, fluorescein, fluorescein isothiocyanate), luminescent materials (e.g., luminol), bioluminescent materials (e.g., luciferase, luciferin), and radioactive materials (e.g., $^{125}$I, $^{131}$I, $^{35}$S or $^{3}$H).

Diagnostic and Prophylactic Formulations hENT1 monoclonal antibodies of the invention are used in diagnostic and prophylactic formulations. In one embodiment, a hENT1 antibody is used to identify patients or patient samples where hENT1 expression and/or activity is low or otherwise reduced. In one embodiment, a hENT1 antibody of the invention is used to identify patients that are more likely to have successful treatment of a cancer or other neoplastic disorder based on the detected hENT1 expression and/or activity level. In one embodiment, a hENT1 antibody of the invention is used to identify patients that are at risk of developing a disorder associated with aberrant hENT1 expression and/or activity. In one embodiment, a hENT1 antibody of the invention is administered to patients that are at risk of developing a disorder associated with aberrant hENT1 expression and/or activity. A patient's or organ's predisposition to one or more of these disorders can be determined using genotypic, serological or biochemical markers such as, for example, hENT1 expression and/or activity level.

Antibodies of the invention are also useful in the detection of hENT1 in patient samples and accordingly are useful as diagnostics. For example, the hENT1 antibodies of the invention are used in in vitro assays, e.g., ELISA, to detect hENT1 levels in a patient sample.

In one embodiment, a hENT1 antibody of the invention is immobilized on a solid support (e.g., the well(s) of a microtiter plate). The immobilized antibody serves as a capture antibody for any hENT1 that may be present in a test sample. The level of detectable label is measured, and the concentration of hENT1 antigen in the test sample is determined by comparison with a standard curve developed from the standard samples.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples, including the experiments conducted and results achieved are provided for illustrative purposes only and are not to be construed as limiting upon the present invention.

Example 1

Anti-hENT1 Antibody Generation and Sequencing

Antibodies were generated as described in Jennings et al., "Distinct regional distribution of human equilibrative nucleoside transporter proteins 1 and 2 (hENT1 and hENT2) in the central nervous system," Neuropharmacology, vol. 40(5): 722-731 (2001), the contents of which are hereby incorporated by reference in their entirety. Briefly, monoclonal antibodies specific for the hENT1 protein were produced by immunization of mice with a synthetic peptide that corresponded to amino acids 254-271 of the predicted intracellular loop between transmembrane segments 6 and 7 of hENT1 and was conjugated to keyhole limpet hemocyanin (KLH). The synthetic peptide-KLH conjugate, purified to >95% homogeneity, was from the Alberta Peptide Institute (University of Alberta, Canada). Monoclonal antibody production followed the procedures of Harlow and Lane ("Antibodies: a Laboratory Manual," Harlow and Lane (eds.) (1988)). Hybridomas were: (i) produced by fusion of splenocytes with the murine myeloma non-secreting cell line, PC/NSI/1-AG4-1; (ii) selected by their ability to grow in 100 µM hypoxanthine, 16 µM aminopterin and 0.4 µM thymidine; and (iii) maintained in growth medium that consisted of RPMI 1640 supplemented with 20% heat-inactivated fetal bovine serum. The supernatants from hybridoma cultures were screened for immunoreactivity by enzyme-linked immunoabsorbent assay (ELISA) using the synthetic peptide (hENT1 amino acids 254-271) conjugated to bovine serum albumin. Hybridoma cultures that exhibited a strong positive result on ELISA in three separate assays were subjected to limiting dilution to obtain clonal populations. Supernatants from the hybridoma cultures that produced monoclonal antibodies with high specificity and avidity for hENT1 protein were collected, centrifuged at 1000 g for 10 minutes to remove any cellular debris and stored at −20° C. until use.

mRNA was extracted from the hybridoma cell pellets, and total RNA was extracted from the pellets. RT-PCR was performed on the extracted RNA. Briefly, cDNA was created from the RNA by reverse-transcription with an oligo(dT) primer. PCR reactions using variable domain primers to amplify both the VH and VL regions of the monoclonal antibody DNA. The VH and VL bands were isolated, and the VL band was gel purified. Both the VL and VH PCR products were cloned into the Invitrogen sequencing vector pCR2.1 (Invitrogen by Life Technologies, Carlsbad Calif.) and transformed into TOP10 *E. coli* cells (Invitrogen by Life Technologies, Carlsbad Calif.) for positive transformants. Selected colonies, VH3-12, VH5-9, VH5-12, VH5-13, VH1-1, VH1-4, VH1-6, VH4-2, VH4-3, VH4-4, VL2, VL10, VL11, VL20, VL21, VL2-2, VL2-3, VL2-7, VL2-10, VL2-12 and VL2-16 were picked and analyzed through sequencing. These VH and VL sequences are described above.

Antibodies were tested for binding and functional activity using the assays described herein. Briefly, the expression of antibody is qualified and quantified using sandwich ELISA. A calibration standard is established using mouse Sigma IgG1 Kappa (Sigma-Aldrich, St. Louis, Mo.). The absorbance is measured at wavelength 450 nM, and the amount of mouse IgG1 Kappa is determined. A second ELISA is then used to demonstrate the affinity of the hENT1 antibody to the hENT1 polypeptide of amino acids 254-271 conjugated to bovine serum albumin. A secondary antibody (goat anti mouse IgG conjugated to horse radish peroxidase) is used and the ELISA plates are read at 450 nM.

Example 2

Expression of Anti-hENT1 Antibodies

The studies described herein demonstrate the expression of anti-hENT1 IgG$_1$ antibodies produced by transfection of CHO cells.

In the first study, following heavy and light chain amino acid sequences were synthesized and cloned into the antibody expression plasmid shown in FIG. 1. The DNA coding for the antibody light chain and heavy chain above was synthesized and optimized for expression in CHO cells by Geneart (Germany). The DNA was inserted into a DHFR expression vector. This vector can also be used for the development of a stable cell line, by selection with Neomycin/G418 antibiotic and/or methotrexate (a DHFR inhibitor).

```
Heavy chain amino acid sequence (SEQ ID NO: 54)

MECTWVILFLLSVIAGVQSQVHLQQSGAELVRPGASVTLPCKASGYTFTDYEMHWVKQTPVHGL

EWIGAIDPETGAIVYNQKFKGKATLTADKSSNTAYMELRSLTSEDSAVYYCTREFTYWGQGTLV

TVSAAKTTPPSVYPLAPGSAAQTNSMVTLGCLVKGYFPEPVTVTWNSGSLSSGVHTFPAVLQSD

LYTLSSSVTVPSSPRPSETVTCNVAHPASSTKVDKKIVPRDCGCKPCICTVPEVSSVFIFPPKP

KDVLTITLTPKVTCVVVDISKDDPEVQFSWFVDDVEVHTAQTQPREEQFNSTFRSVSELPIMHQ

DWLNGKEFKCRVNSAAFPAPIEKTSIKTKGRPKAPQVYTIPPPKEQMAKDKVSLTCMITDFFPE

DITVEWQWNGQPAENYKNTQPIMNTNGSYFVYSKLNVQKSNWEAGNTFTCSVLHEGLHNHHTEK

SLSHSPGK
```

-continued

Light chain amino acid sequence (SEQ ID NO: 55)

MKLPVRLLVLMFWIPASSSDVLMTQTPLTLSVTIGQPASVSCRSSQSLLFSNGKTYLNWLFQRP

GQSPKRLIYLVSKLNSGVPDRFTGTGSGTDFSLKISRVEAEDLGVYYCVQGTHFPWTFGGGTKL

EIKRADAAPTVSIFPPSSEQLTSGGASVVCFLNNFYPKDINVKWKIDGSERQNGVLNSWTDQDS

KDSTYSMSSTLTLTKDEYERHNSYTCEATHKTSTSPIVKSFNRNEC

The variable domains of the heavy and light chains are shown in bold in SEQ ID NO: 54 (heavy chain) and SEQ ID NO: 55 (light chain). The complementarity determining regions (CDRs) are shown in boxes in SEQ ID NO: 54 (heavy chain) and SEQ ID NO: 55 (light chain). CDR sequences were identified using IMGT algorithms as described herein.

Several transfections were carried out on the antibody expression plasmid, under varying conditions in order to optimize the transfection efficiency. Transient transfection (CHO method) was performed as follows: (1) CHO—S cells were cultured in PROCHO4 CDM medium (Lonza); (2) On the day of transfection the cells were centrifuged at 200 g for 5 min and resuspended in fresh UltraCHO/PROCHO5 CDM medium (Lonza) at a cell density of $2\times10^6$ cells/ml; (3) Transfection of culture was performed in a spinner flask using 2.5 µg of DNA and either 4 to 1 or 6 to 1 of PEI to DNA ratio per 1 ml of culture, diluted in 150 mM NaCl; (4) After 5 h, the transfected culture were diluted with 500 ml of fresh Ultra-CHO/ProCHO5 medium and incubated at 37° C. in 6% $CO_2$ with agitation at 88 rpm; and (5) The supernatant was collected after 7-12 days post-transfection.

The following additional transient transfections were also run:

Transient Transfection with PEI 4:1 Ratio:

The transfection was carried out in UltraCHO medium at a volume size of 600 ml in a spinner flask. A DNA plasmid prep at a concentration of 1 mg/ml was used. Supernatant was harvested eight days later for purification ("Supernatant 1").

Transient Transfection with PEI 4:1 Ratio:

Transfection was repeated with UltraCHO medium at a volume size 932 ml in spinner flask. The same plasmid prep was used as above. Supernatant was harvested eight days later for purification.

Transient Transfection with PEI 4:1 Ratio:

Transfection was carried out in 700 ml UltraCHO medium with fresh Maxiprep at a concentration of 2470 µg/ml and purity of 1.7. Supernatant was collected and frozen 11 days later for further purification ("Supernatant 2")

Transient Transfection with PEI 4:1 Ratio:

Transfection was repeated with the same Maxiprep used above in 1000 ml UltraCHO medium. Supernatant was harvested seven days later for purification ("Supernatant 3").

Transient Transfection with PEI 6:1 Ratio:

Modifications were made on the PEI and DNA ratio, which changed from 4:1 to 6:1 ratio, and ProCHO5 medium was used along with UltraCHO medium to compare expression. Concentration of the plasmid prep was 1770 µg/ml and purity was 1.7. Transfections were carried out in volume 700 ml UltraCHO and 500 ml ProCHO5 in spinner flasks. Supernatants were harvested seven days later for purification.

Transient Transfection with PEI 6:1 Ratio:

Transfection was carried out on 480 ml ProCHO5 medium in three separate Erlenmeyer flasks. The concentration of plasmid prep was 1135 µg/ml and purity was 1.61. Supernatant was harvested several days later.

Transient Transfection with PEI 6:1 Ratio:

Transfection was carried out on 200 ml ProCHO5 medium in an Erlenmeyer flasks. The concentration of plasmid prep was 370 µg/ml and purity was 1.5.

Transient Transfection with PEI 6 to 1 Ratio:

Transfection volume was 500 ml in ProCHO5 medium on Erlenmeyer flasks. The concentration of plasmid prep was 3645 µg/ml and purity was 1.7.

The expressed antibody has been detected in the media, and the expressed antibody has been confirmed as anti-hENT1 by ELISA.

The anti-hENT1 antibody was purified from 2 batches of cell culture supernatant of 200 ml and 500 ml using IgG binding buffers. The purifications successfully yielded anti-hENT1 antibody, as demonstrated by Western blot. However, there was also a protein band around 100 kDa in the purified sample.

Figure 2:
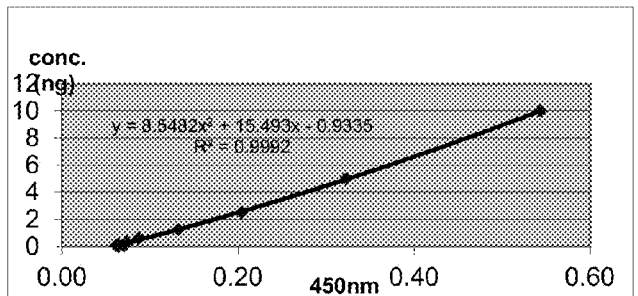
FIG. 2 is a graph depicting the results of a quantitative ELISA assay using standard murine IgG.

Supernatants from several transfections described above were tested by quantitative ELISA along with murine IgG positive control (Sigma-IgG from murine serum). The tested supernatants are referred to herein as "Supernatant 1," "Supernatant 2," and "Supernatant 3." The ELISA plate (Nunc Maxisorp) was coated with goat anti mouse IgG antibodies (Sigma) at concentration 100 ng/well overnight at 4° C. The plate was then blotted with 3% milk (Marvel dried skimmed milk powder) for two hours at room temperature with 150 rpm shaking Murine IgG was prepared in serial dilution from 10 ng/well to 0 ng/well, and added in triplicate to the plate as standard curve. 100 µl of supernatant samples was added in triplicate on the plate. The plate was incubated at room temperature with 150 rpm shaking for two hours and washed with PBS-0.1% Tween 6 times. Anti-mouse IgG antibody (Bio-Rad, Goat Anti-Mouse IgG (H+L)-HRP conjugate) was added for one hour with 150 rpm shaking, then washed with PBS-0.1% Tween 6 times and once with PBS before being developed with TMB. The results of this quantitative ELISA are shown in FIG. 2.

All three supernatants were then tested using a non-reducing western blot methodology. The non-reducing gel was prepared with 12% acrylamide without SDS, and 30 µl of each supernatant samples (Sup. 1, Sup. 2 and Sup. 3) were mixed with treatment buffer at 5:1 dilution respectively (Treatment buffer contained stacking gel buffer, glycerol and double distilled water, SDS or β-mercaptoethanol were removed). Samples mixture were loaded at 30 µl per well. The marker in Lane 1 is See Blue Plus 2 Prestained Standard (1×) (Invitrogen). The gel was then run at 180V for 85 minutes, and transferred to western blot membrane (Amersham Biosciences, Hybond-C Extra) at 20V for 25 minutes. The membrane was blocked with 3% milk (Marvel dried skimmed milk powder) for two hours at room temperature with shaking and probed with anti-mouse IgG antibody (Bio-Rad, Goat Anti-Mouse IgG (H+L)-HRP conjugate) overnight at 4° C. with shaking at 70 rpm. The blot was washed intensively with PBS-0.1% Tween and PBS the next day before developing with ECL solution (Thermo Scientific, SuperSignal West Pico Chemiluminescent substrate) for 1 to 5 mins.

Figure 3:
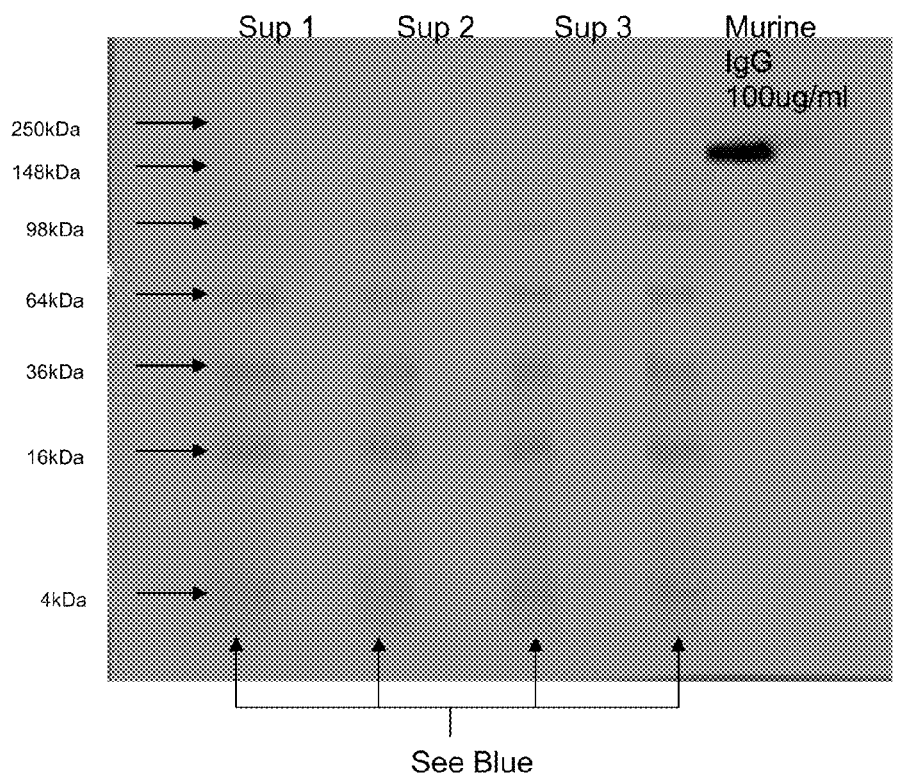
FIG. 3 is an illustration depicting the results of non-reducing western blot analysis of unconcentrated supernatant and positive control murine IgG after 1 min exposure.
Figure 4:
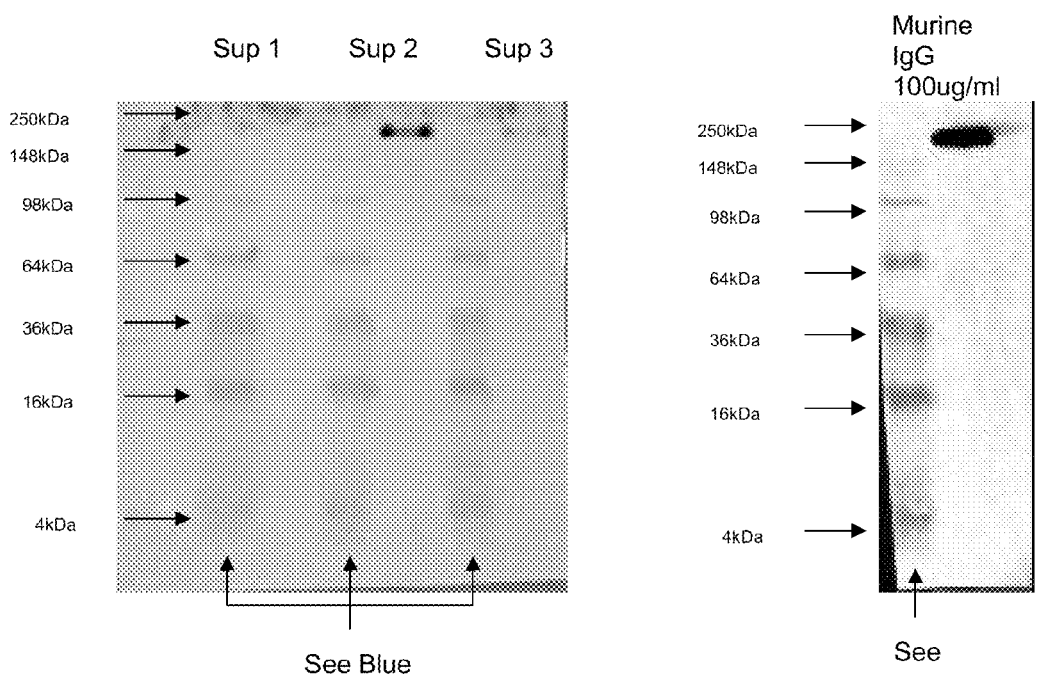
FIG. 4 is an illustration depicting the results of non-reducing western blot analysis, where the blot was over-developed to show positive bands in the supernatants after 5 min exposure.

As shown in FIG. 3, a band was visible between 148 kDa and 250 kDa bands in Supernatant 2 and at the same size in the positive control murine IgG (FIG. 3). Due to the saturation of murine IgG control, the western blot was developed again without the murine IgG (FIG. 4).

Bands are visible in both Supernatant 2 and Supernatant 3. The band in the Supernatant 2 sample appeared to be strongest after being over-developed, and a weak band was visible in the Supernatant 3 sample. This correlated with the concentrations determined by quantitative ELISA in FIG. 2. Both sample bands came up in the unconcentrated supernatants at the same size as the band in the murine IgG positive control.

Intensity of the supernatant bands on the non-reducing western blot corresponds to the concentration showed on quantitative ELISA. Supernatant 2 sample had the highest concentration of IgG and showed the strongest band on western blot, Supernatant 3, which contained less IgG, showed a weak band on blot; and Supernatant 1 contained the lowest concentration of IgG showed no band at all. The variation among these supernatants could be due to the transfection efficiency and IgG expression. Supernatant samples 2 and 3 were transfected with the same DNA preparation which could explain the relatively higher expression levels.

Bands were visible in Supernatant 2 and 3 samples 10 at the same size as the positive control murine IgG by non-reducing western blot. Intact recombinant murine IgG has been produced by transient transfection in CHO cells at a maximal concentration of 466 µg/L.

The isotype of the expressed, recombinant anti-hENT1 antibody was determined using BioAssay Works lateral flow Mouse Iso-Gold test kits (KSOT-001). Briefly 5 µl of antibody samples from two different batches were added to 0.5 ml of sample diluent (ISOT-003) according to the manufacturer's instructions for the testing of "Cell culture/supernatant fluid"; 150 µl of the diluted samples were then added to the three lateral flow cartridges (ISOT-005) and the results were read at 5 minutes. There was a weak result, indicative of low antibody concentration, for both samples for mouse $IgG_1$ with a kappa light chain, the correct isotype to mimic the product of the 10D7G2 hybridoma. No contaminant isoforms were observed.

Expression of the murine IgG1 anti-hENT1 antibody was demonstrated using a sandwich ELISA. Carbonate bicarbonate coating buffer was prepared according to the manufacturer's prescription (1 tablet per 100 ml) using Fluka carbonate bicarbonate buffer tablets. 100 µl of goat anti mouse IgG antibody (Bethyl) was diluted with 10 ml of the pH 9.6 coating buffer. A Greiner 96 well medium bind ELISA plate was coated at 100 µl per well with the anti mouse IgG plate coating antibody solution. The plate was wrapped in parafilm and placed at 2-8° C. overnight.

On the next day, blocking solution was made by preparing Sigma gelatin at 1.5% w/v in carbonate coating buffer. The 96 well plate was removed from the refrigerator, residual binding sites in the plate wells were blocked by adding 200 µl per well of the 1.5% w/v blocking solution. The plate was placed at 37(±2)° C. for approximately 60 minutes.

ELISA wash solution (Phosphate buffered saline, 0.05% Tween 20; PBST) was prepared by dissolving one Fluka Phosphate buffered saline tablet in 500 ml of purified water. Calibrator/sample diluent was prepared by dissolving Sigma gelatin at 1.0% w/v in PBST.

The calibration curve was prepared using Sigma $IgG_1$ Kappa with a declared concentration of 1.0 mg/ml (96.8% purity). A 1/6667 dilution of the 1 mg/ml stock $IgG_1$ was prepared to give the top calibration standard of 150 ng/ml, this standard was serially diluted 1:1 with assay diluent to make the calibration series 150, 75, 38.5, 18.75, 9.375 ng/ml mouse $IgG_1$. Based on the protein concentrations for the purified antibody samples (Sample 1-0.12 mg/ml, Sample 2-0.14 mg/ml), the samples were diluted 1/5000 for testing. The blocking solution was removed from the plate and the wells were washed once at 250 µl/well with assay diluent (PBST 1% gelatin). The calibration standards and media test samples were applied to the plate in triplicate at 100 µl/well. The plate was covered with parafilm, placed onto the plate shaker at a setting of 6/10 for 120 minutes.

At the end of the sample incubation period, the standards and samples were removed and the plate was washed three times at 250 µl/well with assay diluent. The secondary antibody (goat anti mouse IgG conjugated to horse radish peroxidase [HRP], Bethyl) was prepared at a 1/100,000 dilution in assay diluent. The wash was removed and the secondary antibody was added to the plate at 100 µl/well. The plate was covered with parafilm, and placed back onto the plate shaker at a speed of 6/10 for a further 90 minutes.

At the end of the conjugate incubation, the secondary antibody solution was removed and the plate was washed three times with PBST buffer at 250 µl/well, and then rinsed once with purified water. Tetra methyl benzidine (TMB) substrate (Sigma) was added to the plate wells at 100 µl/well. A fresh piece of parafilm was used to cover the plate, which was incubated static at ambient laboratory temperature for 10 minutes. The enzyme-substrate reaction was terminated by adding 100 µl/well of 1M phosphoric acid. The plates were read at 450 nM.

The $A_{450/600}$ for both samples was just detectable above baseline but well below the result for the 9.375 ng/ml calibration standard. The Mouse $IgG_1$ kappa ELISA correlates with the isotype result, both samples contain very low concentrations of this isoform of the antibody.

Affinity of the expressed anti-hENT1 antibodies was demonstrated by ELISA. The 10D7G2 monoclonal antibody was generated using a synthesized peptide sequence of the hENT-1 protein. A second ELISA was performed to test the affinity of the purified recombinant antibody for this synthetic peptide sequence Ac-SKGEEPRAGKEESGVSC-amide (SEQ ID NO: 56).

Carbonate bicarbonate coating buffer was prepared as described for the IgG ELISA above. A vial of the synthetic peptide coupled to BSA(AC-SKGEEPRAGKEESGVSVSC-amide (SEQ ID NO: 59), MW: 1977, Mgs 0.25, coupled to BSA in 1 mg/1 ml PBS) was reconstituted using 250 µl of the carbonate bicarbonate coating buffer to give a theoretical concentration of 1 mg/ml. This was further diluted 1/500 in the carbonate bicarbonate plate coating buffer to give 12 ml of coating solution at 2 µg/ml. A Greiner 96 well medium bind ELISA plate was coated at 100 µl per well with the 2 µg/ml BSA-peptide solution. The plate was wrapped in parafilm and placed at 2-8° C. overnight.

On the next day, blocking solution was made by preparing Sigma gelatin at 1.5% w/v in carbonate coating buffer. The 96 well plate was removed from the refrigerator, residual binding sites in the plate wells were blocked by adding 200 µl per well of the 1.5% w/v blocking solution. The plate was placed at 37(±2)° C. for approximately 60 minutes. PBST wash buffer and assay diluent (1% gelatin in PBST) were prepared as described for the IgG ELISA above. The 1/5000 dilutions of purified IgG samples 1 and 2 were prepared as for the IgG sandwich ELISA described above. The blocking solution was removed from the plate wells; the plate was washed once at 250 µl/well with the assay diluent.

The test samples were applied to plate wells in triplicate at 100 µl/well. The plate was covered with parafilm and placed onto the plate shaker (MPS1) at ambient temperature with shaking at 6/10 for 120 minutes. At the end of the sample incubation, the samples were removed from the wells and the plate was washed three times at 250 µl/well with assay diluent.

The secondary antibody (goat anti mouse IgG conjugated to horse radish peroxidase [HRP], Bethyl) was prepared at a 1/100,000 dilution in assay diluent. The wash was removed and the secondary antibody was added to the plate at 100 µl/well. The plate was covered with parafilm, and placed back onto the plate shaker at a speed of 6/10 for a further 90 minutes. At the end of the conjugate incubation, the secondary antibody solution was removed and the plate was washed three times with PBST buffer at 250 µl/well, and then rinsed once with purified water.

Tetra methyl benzidine (TMB) substrate (Sigma) was added to the plate wells at 100 µl/well. The plate was covered with a fresh piece of parafilm and was incubated static at ambient laboratory temperature for 10 minutes. The enzyme-substrate reaction was terminated by adding 100 µl/well of 1M phosphoric acid. The plates were read at 450 nM.

It is the results of the peptide ELISA that can be used to demonstrate the expression of functional anti peptide IgG by the transient CHO culture. To demonstrate the specificity of the peptide ELISA, 150 ng/ml Sigma IgG1 kappa standard was added to wells D10-12, the results for this sample are insignificantly different to the values recorded for the six wells of assay diluent only (B10-12 & C10-12). Whilst the concentration of the "negative control" was 5000 fold higher than that of the test samples at 150 ng/ml, there is no risk that this would result in a false negative (hook/prozone effect), 150 ng/ml is the top standard used for the mouse IgG1 sandwich ELISA, which uses the same plate type, sample diluent, conjugate wash solution and substrate. It is concluded therefore that any signal generated by a test sample is the result of binding to the peptide sequence only, and not any non specific interaction of mouse IgG1 with the 96 well plate.

Although the signal generated by the two test samples were relatively low they were sufficiently greater than the mouse IgG1 kappa control to conclude that both samples contain recombinant antibody with specific affinity for the synthetic peptide sequence Ac-SKGEEPRAGKEESGVSC-amide (SEQ ID NO: 56).

In an attempt to generate a stronger positive result with the peptide ELISA, 150 ml of conditioned (non-purified) media from a transient culture was used. Using an Amicon stirred cell model 8400 fitted with a YM 10 ultrafiltration disc, the 150 ml volume was reduced to approximately 1.5 ml (100 fold concentration). The concentrated sample was then tested using the peptide ELISA (method and materials as described above) at dilutions of 1/10 to 1/640. The plate reader output demonstrated full functionality of the recombinant antibody expressed during this transient culture against the synthetic peptide sequence.

The testing (isotype, mouse $IgG_1$ and peptide ELISAs and western blot) have demonstrated that the sequence of the variable region, derived from the 10D7G2 hybridoma cells has been accurately determined, transferred into a plasmid construct and transiently expressed within a CHO host cell line.

The sequences described herein have, therefore, been demonstrated to have specific affinity for the synthetic peptide sequence Ac-SKGEEPRAGKEESGVSC-amide (SEQ ID NO: 56).

Figure 5:
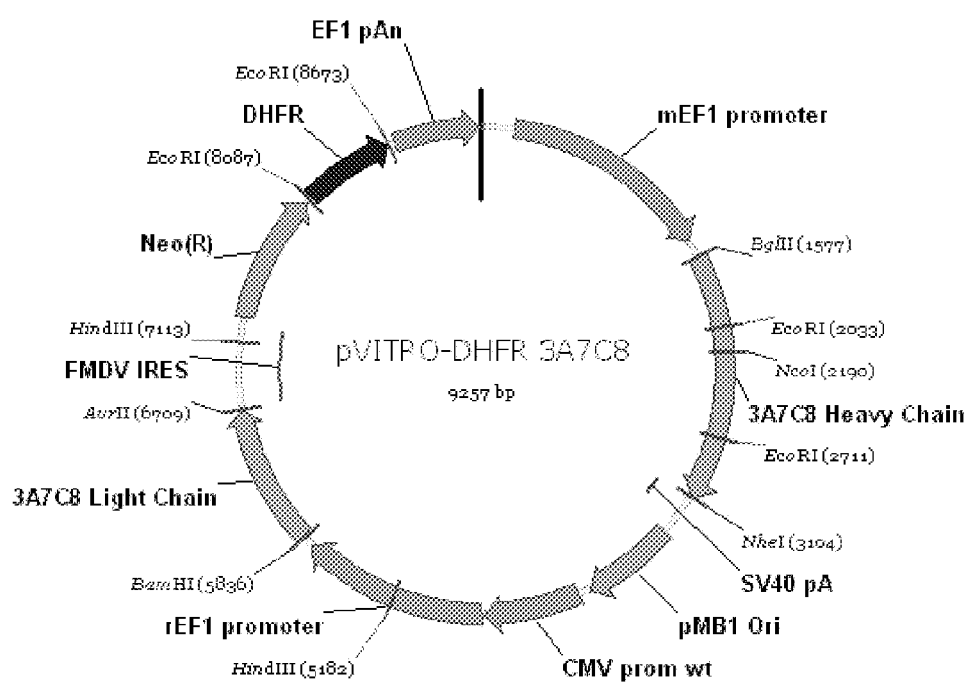
FIG. 5 is a schematic representation of the expression vector used to express additional anti-hENT1 antibodies.

In the second study, the following heavy and light chain amino acid sequences derived from the 3A7C8 hybridoma cells were synthesized and cloned into the antibody expression plasmid shown in FIG. 5. The DNA coding for the antibody light chain and heavy chain above was synthesized and optimized for expression in CHO cells by Geneart (Germany). The DNA was inserted into a DHFR expression vector via restriction sites BamHI and AvrII for the light chain and BglII and NheI for the heavy chain. This vector can also be used for the development of a stable cell line, by selection with Neomycin/G418 antibiotic and/or methotrexate (a DHFR inhibitor).

```
Heavy chain amino acid sequence (SEQ ID NO: 57)

MKCSWVFLFLLSVIAGVQSQVQLQQSGSELVRPGASVTLSCKASGYTFTDYEMHWVKQTPVHGL

EWIGAIDPETGKTAYNQKFKGKTTLTADKSSSTAYMEFRSLTSEDSAVHYCTRELTYWGQGTLV

TVSAAKTTPPSVYPLAPGSAAQTNSMVTLGCLVKGYFPEPVTVTWNSGSLSSGVHTFPAVLQSD

LYTLSSSVTVPSSPRPSETVTCNVAHPASSTKVDKKIVPRDCGCKPCICTCPEVSSVFIFPPKP

KDVLTITLTPKVTCVVVDISKDDPEVQFSWFVDDVEVHTAQTQPREEQFNSTFRSVSELPIMHQ

DWLNGKEFKCRVNSAAFPAPIEKTISKTKGRPKAPQVYTIPPPKEQMAKDKVSLTCMITDFFPE

DITVEWQWNGQPAENYKNTQPIMNTNGSYFVYSKLNVQKSNWEAGNTFTCSVLHEGLHNHHTEK

SLSHSPGK

Light chain amino acid sequence (SEQ ID NO: 55)

MKLPVRLLVLMFWIPASSSDVLMTQTPLTLSVTIGQPASVSCRSSQSLLFSNGKTYLNWLFQRP

GQSPKRLIYLVSKLNSGVPDRFTGTGSGTDFSLKISRVEAEDLGVYYCVQGTHFPWTFGGGTKL

EIKRADAAPTVSIFPPSSEQLTSGGASVVCFLNNFYPKDINVKWKIDGSERQNGVLNSWTDQDS

KDSTYSMSSTLTLTKDEYERHNSYTCEATHKTSTSPIVKSFNRNEC
```

The variable domains of the heavy and light chains are shown in bold in SEQ ID NO: 57 (heavy chain) and SEQ ID NO: 55 (light chain). The complementarity determining regions (CDRs) are shown in boxes in SEQ ID NO: 54 (heavy chain) and SEQ ID NO: 55 (light chain). CDR sequences were identified using IMGT algorithms as described herein.

Several transfections will be carried out on the antibody expression plasmid, under varying conditions in order to optimize the transfection efficiency. For example, this plasmid will be tested using the transient transfection methods described above.

Testing has been performed to confirm that the antibodies derived from the 3A7C8 hybridoma cells has been accurately determined, and further tests, for example, the tests described above in connection with the sequences of the variable region derived from the 10D7G2 hybridoma cells will demonstrate that the antibody expression plasmid shown in FIG. 5 has successfully been transiently expressed within a CHO host cell line.

The invention having now been described by way of written description and example, those of skill in the art will recognize that the invention can be practiced in a variety of embodiments and that the description and examples above are for purposes of illustration and not limitation of the following claims.

What is claimed is:

1. An isolated monoclonal anti-human Equilibrative Nucleoside Transporter 1 (hENT1) antibody or antigen-binding fragment thereof, wherein said antibody comprises:
   (a) a variable heavy chain complementarity determining region 1 (VH CDR1) sequence comprising the amino acid sequence GYTFTDYE (SEQ ID NO: 10);
   (b) a variable heavy chain complementarity determining region 2 (VH CDR2) sequence comprising the amino acid sequence IDPETGAI (SEQ ID NO: 11);
   (c) a variable heavy chain complementarity determining region 3 (VH CDR3) sequence comprising the amino acid sequence TREFTY (SEQ ID NO: 12);
   (d) a variable light chain complementarity determining region 1 (VL CDR1) sequence comprising the amino acid sequence QSLLFSNGKTY (SEQ ID NO: 24);
   (e) a variable light chain complementarity determining region 2 (VL CDR2) sequence comprising the amino acid sequence LVS (SEQ ID NO: 25); and
   (f) a variable light chain complementarity determining region 3 (VL CDR3) sequence comprising the amino acid sequence VQGTHFPWT (SEQ ID NO: 26)
   wherein said antibody or antigen-binding fragment thereof binds hENT1.

2. The antibody of claim 1, wherein said antibody or antigen-binding fragment thereof comprises a heavy chain variable sequence comprising an amino acid sequence selected from SEQ ID NO: 2, 4, 6, 8, 9, 51, 53, and the heavy chain variable domain of SEQ ID NO: 54 comprising residues 17-148 of SEQ ID NO: 54, and wherein said antibody or antigen-binding fragment thereof comprises a light chain variable sequence comprising the amino acid sequence selected from SEQ ID NO: 14, 16, 18, 20, 22, 23, 43, 45, 47, 49, and the light chain variable domain of SEQ ID NO: 55 comprising residues 20-132 of SEQ ID NO: 55.

3. The antibody of claim 1, wherein said antibody is an IgG isotype or antigen-binding fragment of an IgG isotype antibody.

4. The antibody of claim 3, wherein said antibody is an IgG1 isotype or antigen-binding fragment of an IgG1 isotype antibody.

5. The antibody of claim 4, wherein said antibody is an IgG1 kappa isotype or antigen-binding fragment of an IgG1 kappa isotype antibody.

6. An isolated monoclonal antibody or antigen-binding fragment thereof comprising a heavy chain variable sequence comprising the amino acid sequence of SEQ ID NO: 2, 4, 6, 8, 9, 51, 53, and the heavy chain variable domain of SEQ ID NO: 54 comprising residues 17-148 of SEQ ID NO: 54 and a light chain variable sequence comprising the amino acid sequence of SEQ ID NO: 14, 16, 18, 20, 22, 23, 43, 45, 47 and 49 or the light chain variable domain of SEQ ID NO: 55 comprising residues 20-132 of SEQ ID NO: 55, wherein said antibody or antigen-binding fragment thereof binds human Equilibrative Nucleoside Transporter 1 (hENT1).

7. The antibody of claim 6, wherein said antibody is an IgG isotype or antigen-binding fragment of an IgG isotype antibody.

8. A pharmaceutical composition comprising the antibody or antigen-binding fragment thereof of claim 1 and a carrier.

9. A pharmaceutical composition comprising the antibody or antigen-binding fragment thereof of claim 6 and a carrier.

* * * * *